US005716804A

United States Patent [19]

Moore et al.

[11] Patent Number: 5,716,804

[45] Date of Patent: Feb. 10, 1998

[54] MAMMALIAN INTERLEUKIN-10 (IL-10) SUPER-ACTIVATING RECEPTORS; AND VARIANTS

[75] Inventors: Kevin W. Moore, Palo Alto; Sherry Wei, San Jose; Alice Suk-Yue Ho, Union City, all of Calif.

[73] Assignee: Schering Corporation, Kenilworth, N.J.

[21] Appl. No.: 424,788

[22] Filed: Apr. 19, 1995

[51] Int. Cl.[6] .......................... C07K 14/705; C12N 15/12

[52] U.S. Cl. .................. 435/69.1; 435/252.3; 435/320.1; 435/6; 435/7.1; 530/350; 536/23.5

[58] Field of Search ................................ 435/69.1, 252.3, 435/320.1, 6, 7.1; 530/350; 536/23.5

[56] References Cited

PUBLICATIONS

J. Fernando Bazan "Structural design and molecular evolution of a cytokine receptor superfamily," *Proc. Natl. Acad. Sci.* 87:6934–6938, Sep. 1990.

J. Fernando Bazan "Haematopoietic receptors and helical cytokines," *Immunol. Today* 11:350–354, 1990.

Alan D. D'Andrea, et al. "The Cytoplasmic Region of the Erythropoietin Receptor Contains Nonoverlapping Positive and Negative Growth–Regulatory Domains," *Molec. Cell. Biol.* 11:1980–1987, Apr. 1991.

René de Waal Malefyt, et al. "Interleukin 10 (IL–10) Inhibits Cytokine Synthesis by Human Monocytes: An Autoregulatory Role of IL–10 Produced by Monocytes," *J. Exp. Med.* 174:1209–1220, Nov. 1991.

David F. Fiorentino, et al. "Two Types of Mouse Helper Cell," *J. Exp. Med.* 170:2081–2095, Dec. 1989.

David F. Fiorentino, et al. "IL–10 Inhibits Cytokine Production by Activated Macrophages," *J. Immunol.* 147:3815–3822, Dec. 1991.

David P. Gearing, et al. "Expression cloning of a receptor for human granulocyte–macrophage colony–stimulating factor," *EMBO J.* 8:3667–3676, 1989.

Kazuniro Hayashida, et al. "Molecular cloning of a second subunit of the receptor for human granulocyte–macrophage colony–stimulating factor (GM–CSF): Reconstitution of a high–affinity GM–CSF receptor," *Proc. Natl. Acad. Sci.* 87:9655–9659, Dec. 1990.

Alice Suk Yue Ho, et al. "A receptor for interleukin 10 is related to interferon receptors," *Proc. Natl. Acad. Sci.* 90:11267–11271, Dec. 1993.

Alice Suk Yue Ho, et al. "Interleukin–10 and its receptor," *Ther. Immunol.* 1:173–185, 1994.

Alice S.Y. Ho, et al. "Structural and Functional Studies of Interleukin–10 Receptors," Abstract #4315 from the American Association of Immunology Meeting, Apr. 1994.

Di–Hwei Hsu, et al. "Expression of Interleukin–10 Activity by Epstein–Barr Virus Protein BCRF1," *Science* 250:830–832, Nov. 1990.

Di–Hwei Hsu, et al. "Defferential effects of IL–4 and IL–10 on IL–2–induced IFN–γ synthesis and lymphokine–activated killer activity," *Intl. Immunol.* 4:563–569, 1992.

Naoto Itoh, et al. "Cloning of an Interleukin–3 Receptor Gene: A Member of a Distinct Receptor Gene Family," *Science* 247:324–327, Jan. 1990.

Atsushi Miyajima, et al. "Common subunits of cytokine receptors and the functional redundancy of cytokines," *TIBS* 17:378–382, Oct. 1992.

Andrew C. Larner, et al. "Tyrosine Phosphorylation of DNA Binding Proteins by Multiple Cytokines," *Science* 261:1730–1733, Sep. 1993.

Jörg Lehmann, et al. "IL–10–Induced Factors Belonging to the p91 Family of Proteins Bind to IFN–γ–Responsive Promoter Elements," *J. Immunol.* 165–172, 1994.

Ying Liu, et al. "Expression Cloning and Characterization of a Human IL–10 Receptor," *J. Immunol.* 152:1821–1829, 1994.

Atsushi Miyajima, et al. "Cytokine Receptors and Signal Transduction," *Ann. Rev. Immunol.* 10:295–331, 1992.

Kevin W. Moore, et al. "Homology of Cytokine Synthesis Inhibitory Factor (IL–10) to the Epstein–Barr Virus Gene BCRF1," *Science* 248:1230–1234, Jun. 1990.

Kevin W. Moore, et al. "Interleukin–10," *Ann. Rev. Immunol.* 11:165–190, 1993.

Tim R. Mosmann, et al. "The role of IL–10 in crossregulation of $T_H1$ and $T_H2$ responses," *Immunol. Today* 12:A49–A53, 1991.

Hans–Jürgen Rode, et al. "The Genome of Equine Herpesvirus Type 2 Harbors an Interleukin 10 (IL–10)–Like Gene," *Virus Genes* 7:111–116, 1993.

Kazuhiro Sakamaki, et al. "Critical cytoplasmic domains of the common β subunit of the human GM–CSF, IL–3 and IL–5 receptors for growth signal transduction and tyrosine phosphorylation," *EMBO J.* 111:3541–3549, 1992.

Noriko Sato, et al. "Signal transduction by the high–affinity GM–SCF receptor: two distinct cytoplasmic regions of the common β subunit responsible for different signaling," *EMBO J.* 12:4181–4189, 1993.

Jimmy C. Tan, et al. "Characterization of Interleukin–10 Receptors on Human and Mouse Cells," *J. Biol. Chem.* 268:21053–21059, Oct. 1993.

Jan Tavernier, et al. "A Human High Affinity Interleukin–5 Receptor (IL5R) Is Composed of an IL5–Specific α Chain and a β Chain Shared with the Receptors for GM–CSF," *Cell* 66:1175–1184, Sep. 1991.

P. Vieira, et al. "Isolation and expressioin of human cytokine synthesis inhibitory factor cDNA clones: Homology to Epstein–Barr virus open reading frame BCRF1," *Proc. Natl. Acad. Sci.* 88:1172–1176, Feb. 1991.

*Primary Examiner*—John Ulm

*Attorney, Agent, or Firm*—Sheela Mohan-Peterson; Edwin P. Ching

[57] ABSTRACT

Amino acid sequence and nucleic acid encoding various functional variants of the IL-10 receptors. Uses of the receptor gene and polypeptides are disclosed, including means for screening for agonists and antagonists of the receptor ligands, for producing diagnostic or therapeutic reagents, and for producing antibodies. Therapeutic or diagnostic reagents and kits are also provided.

26 Claims, 5 Drawing Sheets

Small
Dra III
Y374
Y396
Y427
Y477
Proliferation
Wild-type
ORF +
Δ 380-559 −
Δ 402-559 −
Δ 433-559 +
Δ 483-559 +
Δ 282-389 +
Δ 282-414 +
Δ 282-458 +

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 3520 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 80..1807

( i x ) FEATURE:
( A ) NAME/KEY: mat_peptide
( B ) LOCATION: 128..1807

( x i ) SEQUENCE DESCRIPTION: SEQ ID NO:1:

```
CCATTGTGCT GGAAAGCAGG ACGCGCCGGC CGGAGGCGTA AAGGCCGGCT CCAGTGGACG      60

ATGCCGCTGT GCGCCCAGG ATG TTG TCG CGT TTG CTC CCA TTC CTC GTC ACG      112
                     Met Leu Ser Arg Leu Leu Pro Phe Leu Val Thr
                     -16 -15                 -10

ATC TCC AGC CTG AGC CTA GAA TTC ATT GCA TAC GGG ACA GAA CTG CCA      160
Ile Ser Ser Leu Ser Leu Glu Phe Ile Ala Tyr Gly Thr Glu Leu Pro
 -5                   1               5                  10

AGC CCT TCC TAT GTG TGG TTT GAA GCC AGA TTT TTC CAG CAC ATC CTC      208
Ser Pro Ser Tyr Val Trp Phe Glu Ala Arg Phe Phe Gln His Ile Leu
             15                  20                  25

CAC TGG AAA CCT ATC CCA AAC CAG TCT GAG AGC ACC TAC TAT GAA GTG      256
His Trp Lys Pro Ile Pro Asn Gln Ser Glu Ser Thr Tyr Tyr Glu Val
         30                  35                  40

GCC CTC AAA CAG TAC GGA AAC TCA ACC TGG AAT GAC ATC CAT ATC TGT      304
Ala Leu Lys Gln Tyr Gly Asn Ser Thr Trp Asn Asp Ile His Ile Cys
     45                  50                  55

AGA AAG GCT CAG GCA TTG TCC TGT GAT CTC ACA ACG TTC ACC CTG GAT      352
Arg Lys Ala Gln Ala Leu Ser Cys Asp Leu Thr Thr Phe Thr Leu Asp
 60                  65                  70                  75

CTG TAT CAC CGA AGC TAT GGC TAC CGG GCC AGA GTC CGG GCA GTG GAC      400
Leu Tyr His Arg Ser Tyr Gly Tyr Arg Ala Arg Val Arg Ala Val Asp
                 80                  85                  90

AAC AGT CAG TAC TCC AAC TGG ACC ACC ACT GAG ACT CGC TTC ACA GTG      448
Asn Ser Gln Tyr Ser Asn Trp Thr Thr Thr Glu Thr Arg Phe Thr Val
             95                 100                 105

GAT GAA GTG ATT CTG ACA GTG GAT AGC GTG ACT CTG AAA GCA ATG GAC      496
Asp Glu Val Ile Leu Thr Val Asp Ser Val Thr Leu Lys Ala Met Asp
        110                 115                 120

GGC ATC ATC TAT GGG ACA ATC CAT CCC CCC AGG CCC ACG ATA ACC CCT      544
Gly Ile Ile Tyr Gly Thr Ile His Pro Pro Arg Pro Thr Ile Thr Pro
    125                 130                 135

GCA GGG GAT GAG TAC GAA CAA GTC TTC AAG GAT CTC CGA GTT TAC AAG      592
Ala Gly Asp Glu Tyr Glu Gln Val Phe Lys Asp Leu Arg Val Tyr Lys
140                 145                 150                 155

ATT TCC ATC CGG AAG TTC TCA GAA CTA AAG AAT GCA ACC AAG AGA GTG      640
Ile Ser Ile Arg Lys Phe Ser Glu Leu Lys Asn Ala Thr Lys Arg Val
                160                 165                 170

AAA CAG GAA ACC TTC ACC CTC ACG GTC CCC ATA GGG GTG AGA AAG TTT      688
Lys Gln Glu Thr Phe Thr Leu Thr Val Pro Ile Gly Val Arg Lys Phe
```

-continued

```
                175                          180                          185

TGT GTC AAG GTG CTG CCC CGC TTG GAA TCC CGA ATT AAC AAG GCA GAG         736
Cys Val Lys Val Leu Pro Arg Leu Glu Ser Arg Ile Asn Lys Ala Glu
        190                     195                     200

TGG TCG GAG GAG CAG TGT TTA CTT ATC ACG ACG GAG CAG TAT TTC ACT         784
Trp Ser Glu Glu Gln Cys Leu Leu Ile Thr Thr Glu Gln Tyr Phe Thr
    205                     210                     215

GTG ACC AAC CTG AGC ATC TTA GTC ATA TCT ATG CTG CTA TTC TGT GGA         832
Val Thr Asn Leu Ser Ile Leu Val Ile Ser Met Leu Leu Phe Cys Gly
220                     225                     230                     235

ATC CTG GTC TGT CTG GTT CTC CAG TGG TAC ATC CGG CAC CCG GGG AAG         880
Ile Leu Val Cys Leu Val Leu Gln Trp Tyr Ile Arg His Pro Gly Lys
                240                     245                     250

TTG CCT ACA GTC CTG GTC TTC AAG AAG CCT CAC GAC TTC TTC CCA GCC         928
Leu Pro Thr Val Leu Val Phe Lys Lys Pro His Asp Phe Phe Pro Ala
            255                     260                     265

AAC CCT CTC TGC CCA GAA ACT CCC GAT GCC ATT CAC ATC GTG GAC CTG         976
Asn Pro Leu Cys Pro Glu Thr Pro Asp Ala Ile His Ile Val Asp Leu
        270                     275                     280

GAG GTT TTC CCA AAG GTG TCA CTA GAG CTG AGA GAC TCA GTC CTG CAT        1024
Glu Val Phe Pro Lys Val Ser Leu Glu Leu Arg Asp Ser Val Leu His
    285                     290                     295

GGC AGC ACC GAC AGT GGC TTT GGC AGT GGT AAA CCA TCA CTT CAG ACT        1072
Gly Ser Thr Asp Ser Gly Phe Gly Ser Gly Lys Pro Ser Leu Gln Thr
300                     305                     310                     315

GAA GAG TCC CAA TTC CTC CTC CCT GGC TCC CAC CCC CAG ATA CAG GGG        1120
Glu Glu Ser Gln Phe Leu Leu Pro Gly Ser His Pro Gln Ile Gln Gly
                320                     325                     330

ACT CTG GGA AAA GAA GAG TCT CCA GGG CTA CAG GCC ACC TGT GGG GAC        1168
Thr Leu Gly Lys Glu Glu Ser Pro Gly Leu Gln Ala Thr Cys Gly Asp
            335                     340                     345

AAC ACG GAC AGT GGG ATC TGC CTG CAG GAG CCC GGC TTA CAC TCC AGC        1216
Asn Thr Asp Ser Gly Ile Cys Leu Gln Glu Pro Gly Leu His Ser Ser
        350                     355                     360

ATG GGG CCC GCC TGG AAG CAG CAG CTT GGA TAT ACC CAT CAG GAC CAG        1264
Met Gly Pro Ala Trp Lys Gln Gln Leu Gly Tyr Thr His Gln Asp Gln
    365                     370                     375

GAT GAC AGT GAC GTT AAC CTA GTC CAG AAC TCT CCA GGG CAG CCT AAG        1312
Asp Asp Ser Asp Val Asn Leu Val Gln Asn Ser Pro Gly Gln Pro Lys
380                     385                     390                     395

TAC ACA CAG GAT GCA TCT GCC TTG GGC CAT GTC TGT CTC CTA GAA CCT        1360
Tyr Thr Gln Asp Ala Ser Ala Leu Gly His Val Cys Leu Leu Glu Pro
                400                     405                     410

AAA GCC CCT GAG GAG AAA GAC CAA GTC ATG GTG ACA TTC CAG GGC TAC        1408
Lys Ala Pro Glu Glu Lys Asp Gln Val Met Val Thr Phe Gln Gly Tyr
            415                     420                     425

CAG AAA CAG ACC AGA TGG AAG GCA GAG GCA GCA GGC CCA GCA GAA TGC        1456
Gln Lys Gln Thr Arg Trp Lys Ala Glu Ala Ala Gly Pro Ala Glu Cys
        430                     435                     440

TTG GAC GAA GAG ATT CCC TTG ACA GAT GCC TTT GAT CCT GAA CTT GGG        1504
Leu Asp Glu Glu Ile Pro Leu Thr Asp Ala Phe Asp Pro Glu Leu Gly
    445                     450                     455

GTA CAC CTG CAG GAT GAT TTG GCT TGG CCT CCA CCA GCT CTG GCC GCA        1552
Val His Leu Gln Asp Asp Leu Ala Trp Pro Pro Pro Ala Leu Ala Ala
460                     465                     470                     475

GGT TAT TTG AAA CAG GAG TCT CAA GGG ATG GCT TCT GCT CCA CCA GGG        1600
Gly Tyr Leu Lys Gln Glu Ser Gln Gly Met Ala Ser Ala Pro Pro Gly
                480                     485                     490

ACA CCA AGT AGA CAG TGG AAT CAA CTG ACC GAA GAG TGG TCA CTC CTG        1648
Thr Pro Ser Arg Gln Trp Asn Gln Leu Thr Glu Glu Trp Ser Leu Leu
```

-continued

```
                495                       500                       505

GGT GTG GTT AGC TGT GAA GAT CTA AGC ATA GAA AGT TGG AGG TTT GCC      1696
Gly Val Val Ser Cys Glu Asp Leu Ser Ile Glu Ser Trp Arg Phe Ala
        510                     515                     520

CAT AAA CTT GAC CCT CTG GAC TGT GGG GCA GCC CCT GGT GGC CTC CTG      1744
His Lys Leu Asp Pro Leu Asp Cys Gly Ala Ala Pro Gly Gly Leu Leu
    525                     530                     535

GAT AGC CTT GGC TCT AAC CTG GTC ACC CTG CCG TTG ATC TCC AGC CTG      1792
Asp Ser Leu Gly Ser Asn Leu Val Thr Leu Pro Leu Ile Ser Ser Leu
540                     545                     550                     555

CAG GTA GAA GAA TGACAGCGGC TAAGAGTTAT TTGTATTCCA GCCATGCCTG          1844
Gln Val Glu Glu
                560

CTCCCCTCCC TGTACCTGGG AGGCTCAGGA GTCAAAGAAA TATGTGGGTC CTTTTCTGCA    1904

GACCTACTGT GACCAGCTAG CCAGGCTCCA CGGGGCAAGG AAAGGCCATC TTGATACACG    1964

AGTGTCAGGT ACATGAGAGG TTGTGGCTAG TCTGCTGAGT GAGGGTCTGT AGATACCAGC    2024

AGAGCTGAGC AGGATTGACA GAGACCTCCT CATGCCTCAG GGCTGGCTCC TACACTGGAA    2084

GGACCTGTGT TTGGGTGTAA CCTCAGGGCT TTCTGGATGT GGTAAGACTG TAGGTCTGAA    2144

GTCAGCTGAG CCTGGATGTC TGCGGAGGTG TTGGAGTGGC TAGCCTGCTA CAGGATAAAG    2204

GGAAGGCTCA AGAGATAGAA GGGCAGAGCA TGAGCCAGGT TTAATTTTGT CCTGTAGAGA    2264

TGGTCCCCAG CCAGGATGGG TTACTTGTGG CTGGGAGATC TTGGGGTATA CACCACCCTG    2324

AATGATCAGC CAGTCAATTC AGAGCTGTGT GGCAAAAGGG ACTGAGACCC AGAATTTCTG    2384

TTCCTCTTGT GAGGTGTCTC TGCTACCCAT CTGCAGACAG ACATCTTCAT CTTTTTACTA    2444

TGGCTGTGTC CCCTGAATTA CCAGCAGTGG CCAAGCCATT ACTCCCTGCT GCTCACTGTT    2504

GTGACGTCAG ACCAGACCAG ACGCTGTCTG TCTGTGTTAG TACACTACCC TTTAGGTGGC    2564

CTTTGGGCTT GAGCACTGGC CCAGGCTTAG GACTTATGTC TGCTTTTGCT GCTAATCTCT    2624

AACTGCAGAC CCAGAGAACA GGGTGCTGGG CTGACACCTC CGTGTTCAGC TGTGTGACCT    2684

CCGACCAGCA GCTTCCTCAG GGGACTAAAA TAATGACTAG GTCATTCAGA AGTCCCTCAT    2744

GCTGAATGTT AACCAAGGTG CCCCTGGGGT GATAGTTTAG GTCCTGCAAC CTCTGGGTTG    2804

GAAGGAAGTG GACTACGGAA GCCATCTGTC CCCCTGGGGA GCTTCCACCT CATGCCAGTG    2864

TTTCAGAGAT CTTGTGGGAG CCTAGGGCCT TGTGCCAAGG GAGCTGCTAG TCCCTGGGGT    2924

CTAGGGCTGG TCCCTGCCTC CCTATACTGC GTTTGAGACC TGTCTTCAAA TGGAGGCAGT    2984

TTGCAGCCCC TAAGCAAGGA TGCTGAGAGA AGCAGCAAGG CTGCTGATCC CTGAGCCCAG    3044

AGTTTCTCTG AAGCTTTCCA AATACAGACT GTGTGACGGG GTGAGGCCAG CCATGAACTT    3104

TGGCATCCTG CCGAGAAGGT CATGACCCTA ATCTGGTACG AGAGCTCCTT CTGGAACTGG    3164

GCAAGCTCTT TGAGACCCCC CTGGAACCTT TATTTATTTA TTTGCTCACT TATTTATTGA    3224

GGAAGCAGCG TGGCACAGGC GCAAGGCTCT GGGTCTCTCA GGAGGTCTAG ATTTGCCTGC    3284

CCTGTTTCTA GCTGTGTGAC CTTGGGCAAG TCACGTTTCC TCGTGGAGCC TCAGTTTTCC    3344

TGTCTGTATG CAAAGCTTGG AAATTGAAAT GTACCTGACG TGCTCCATCC CTAGGAGTGC    3404

TGAGTCCCAC TGAGAAAGCG GGCACAGACG CCTCAAATGG AACCACAAGT GGTGTGTGTT    3464

TTCATCCTAA TAAAAGTCA GGTGTTTTGT GGAAAAAAAA AAAAAAAAAA AAAAAA        3520
```

( 2 ) INFORMATION FOR SEQ ID NO:2:

( i ) SEQUENCE CHARACTERISTICS:

( A ) LENGTH: 575 amino acids ( B ) TYPE: amino acid ( D ) TOPOLOGY: linear ( i i ) MOLECULE TYPE: protein ( x i ) SEQUENCE DESCRIPTION: SEQ ID NO:2:

```
Met Leu Ser Arg Leu Leu Pro Phe Leu Val Thr Ile Ser Ser Leu Ser
-16 -15                 -10                 -5

Leu Glu Phe Ile Ala Tyr Gly Thr Glu Leu Pro Ser Pro Ser Tyr Val
1               5                   10                  15

Trp Phe Glu Ala Arg Phe Phe Gln His Ile Leu His Trp Lys Pro Ile
            20                  25                  30

Pro Asn Gln Ser Glu Ser Thr Tyr Tyr Glu Val Ala Leu Lys Gln Tyr
        35                  40                  45

Gly Asn Ser Thr Trp Asn Asp Ile His Ile Cys Arg Lys Ala Gln Ala
    50                  55                  60

Leu Ser Cys Asp Leu Thr Thr Phe Thr Leu Asp Leu Tyr His Arg Ser
65                  70                  75                  80

Tyr Gly Tyr Arg Ala Arg Val Arg Ala Val Asp Asn Ser Gln Tyr Ser
                85                  90                  95

Asn Trp Thr Thr Thr Glu Thr Arg Phe Thr Val Asp Glu Val Ile Leu
            100                 105                 110

Thr Val Asp Ser Val Thr Leu Lys Ala Met Asp Gly Ile Ile Tyr Gly
        115                 120                 125

Thr Ile His Pro Pro Arg Pro Thr Ile Thr Pro Ala Gly Asp Glu Tyr
    130                 135                 140

Glu Gln Val Phe Lys Asp Leu Arg Val Tyr Lys Ile Ser Ile Arg Lys
145                 150                 155                 160

Phe Ser Glu Leu Lys Asn Ala Thr Lys Arg Val Lys Gln Glu Thr Phe
                165                 170                 175

Thr Leu Thr Val Pro Ile Gly Val Arg Lys Phe Cys Val Lys Val Leu
            180                 185                 190

Pro Arg Leu Glu Ser Arg Ile Asn Lys Ala Glu Trp Ser Glu Glu Gln
        195                 200                 205

Cys Leu Leu Ile Thr Thr Glu Gln Tyr Phe Thr Val Thr Asn Leu Ser
    210                 215                 220

Ile Leu Val Ile Ser Met Leu Leu Phe Cys Gly Ile Leu Val Cys Leu
225                 230                 235                 240

Val Leu Gln Trp Tyr Ile Arg His Pro Gly Lys Leu Pro Thr Val Leu
                245                 250                 255

Val Phe Lys Lys Pro His Asp Phe Phe Pro Ala Asn Pro Leu Cys Pro
            260                 265                 270

Glu Thr Pro Asp Ala Ile His Ile Val Asp Leu Glu Val Phe Pro Lys
        275                 280                 285

Val Ser Leu Glu Leu Arg Asp Ser Val Leu His Gly Ser Thr Asp Ser
    290                 295                 300

Gly Phe Gly Ser Gly Lys Pro Ser Leu Gln Thr Glu Glu Ser Gln Phe
305                 310                 315                 320

Leu Leu Pro Gly Ser His Pro Gln Ile Gln Gly Thr Leu Gly Lys Glu
                325                 330                 335

Glu Ser Pro Gly Leu Gln Ala Thr Cys Gly Asp Asn Thr Asp Ser Gly
            340                 345                 350

Ile Cys Leu Gln Glu Pro Gly Leu His Ser Ser Met Gly Pro Ala Trp
        355                 360                 365

Lys Gln Gln Leu Gly Tyr Thr His Gln Asp Gln Asp Asp Ser Asp Val
    370                 375                 380
```

-continued

Asn Leu Val Gln Asn Ser Pro Gly Gln Pro Lys Tyr Thr Gln Asp Ala
385 390 395 400

Ser Ala Leu Gly His Val Cys Leu Leu Glu Pro Lys Ala Pro Glu Glu
405 410 415

Lys Asp Gln Val Met Val Thr Phe Gln Gly Tyr Gln Lys Gln Thr Arg
420 425 430

Trp Lys Ala Glu Ala Ala Gly Pro Ala Glu Cys Leu Asp Glu Glu Ile
435 440 445

Pro Leu Thr Asp Ala Phe Asp Pro Glu Leu Gly Val His Leu Gln Asp
450 455 460

Asp Leu Ala Trp Pro Pro Pro Ala Leu Ala Ala Gly Tyr Leu Lys Gln
465 470 475 480

Glu Ser Gln Gly Met Ala Ser Ala Pro Pro Gly Thr Pro Ser Arg Gln
485 490 495

Trp Asn Gln Leu Thr Glu Glu Trp Ser Leu Leu Gly Val Val Ser Cys
500 505 510

Glu Asp Leu Ser Ile Glu Ser Trp Arg Phe Ala His Lys Leu Asp Pro
515 520 525

Leu Asp Cys Gly Ala Ala Pro Gly Gly Leu Leu Asp Ser Leu Gly Ser
530 535 540

Asn Leu Val Thr Leu Pro Leu Ile Ser Ser Leu Gln Val Glu Glu
545 550 555

( 2 ) INFORMATION FOR SEQ ID NO:3:

( i ) SEQUENCE CHARACTERISTICS:
( A ) LENGTH: 559 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

Leu Glu Phe Ile Ala Tyr Gly Thr Glu Leu Pro Ser Pro Ser Tyr Val
1 5 10 15

Trp Phe Glu Ala Arg Phe Phe Gln His Ile Leu His Trp Lys Pro Ile
20 25 30

Pro Asn Gln Ser Glu Ser Thr Tyr Tyr Glu Val Ala Leu Lys Gln Tyr
35 40 45

Gly Asn Ser Thr Trp Asn Asp Ile His Ile Cys Arg Lys Ala Gln Ala
50 55 60

Leu Ser Cys Asp Leu Thr Thr Phe Thr Leu Asp Leu Tyr His Arg Ser
65 70 75 80

Tyr Gly Tyr Arg Ala Arg Val Arg Ala Val Asp Asn Ser Gln Tyr Ser
85 90 95

Asn Trp Thr Thr Thr Glu Thr Arg Phe Thr Val Asp Glu Val Ile Leu
100 105 110

Thr Val Asp Ser Val Thr Leu Lys Ala Met Asp Gly Ile Ile Tyr Gly
115 120 125

Thr Ile His Pro Pro Arg Pro Thr Ile Thr Pro Ala Gly Asp Glu Tyr
130 135 140

Glu Gln Val Phe Lys Asp Leu Arg Val Tyr Lys Ile Ser Ile Arg Lys
145 150 155 160

Phe Ser Glu Leu Lys Asn Ala Thr Lys Arg Val Lys Gln Glu Thr Phe
165 170 175

-continued

```
Thr Leu Thr Val Pro Ile Gly Val Arg Lys Phe Cys Val Lys Val Leu
            180                 185                 190

Pro Arg Leu Glu Ser Arg Ile Asn Lys Ala Glu Trp Ser Glu Glu Gln
        195                 200                 205

Cys Leu Leu Ile Thr Thr Glu Gln Tyr Phe Thr Val Thr Asn Leu Ser
    210                 215                 220

Ile Leu Val Ile Ser Met Leu Leu Phe Cys Gly Ile Leu Val Cys Leu
225                 230                 235                 240

Val Leu Gln Trp Tyr Ile Arg His Pro Gly Lys Leu Pro Thr Val Leu
                245                 250                 255

Val Phe Lys Lys Pro His Asp Phe Phe Pro Ala Asn Pro Leu Cys Pro
            260                 265                 270

Glu Thr Pro Asp Ala Ile His Ile Val Asp Leu Glu Val Phe Pro Lys
        275                 280                 285

Val Ser Leu Glu Leu Arg Asp Ser Val Leu His Gly Ser Thr Asp Ser
    290                 295                 300

Gly Phe Gly Ser Gly Lys Pro Ser Leu Gln Thr Glu Glu Ser Gln Phe
305                 310                 315                 320

Leu Leu Pro Gly Ser His Pro Gln Ile Gln Gly Thr Leu Gly Lys Glu
                325                 330                 335

Glu Ser Pro Gly Leu Gln Ala Thr Cys Gly Asp Asn Thr Asp Ser Gly
            340                 345                 350

Ile Cys Leu Gln Glu Pro Gly Leu His Ser Ser Met Gly Pro Ala Trp
        355                 360                 365

Lys Gln Gln Leu Gly Tyr Thr His Gln Asp Gln Asp Asp Ser Asp Val
    370                 375                 380

Asn Leu Val Gln Asn Ser Pro Gly Gln Pro Lys Tyr Thr Gln Asp Ala
385                 390                 395                 400

Ser Ala Leu Gly His Val Cys Leu Leu Glu Pro Lys Ala Pro Glu Glu
                405                 410                 415

Lys Asp Gln Val Met Val Thr Phe Gln Gly Tyr Gln Lys Gln Thr Arg
            420                 425                 430

Trp Lys Ala Glu Ala Ala Gly Pro Ala Glu Cys Leu Asp Glu Glu Ile
        435                 440                 445

Pro Leu Thr Asp Ala Phe Asp Pro Glu Leu Gly Val His Leu Gln Asp
    450                 455                 460

Asp Leu Ala Trp Pro Pro Pro Ala Leu Ala Ala Gly Tyr Leu Lys Gln
465                 470                 475                 480

Glu Ser Gln Gly Met Ala Ser Ala Pro Pro Gly Thr Pro Ser Arg Gln
                485                 490                 495

Trp Asn Gln Leu Thr Glu Glu Trp Ser Leu Leu Gly Val Val Ser Cys
            500                 505                 510

Glu Asp Leu Ser Ile Glu Ser Trp Arg Phe Ala His Lys Leu Asp Pro
        515                 520                 525

Leu Asp Cys Gly Ala Ala Pro Gly Gly Leu Leu Asp Ser Leu Gly Ser
    530                 535                 540

Asn Leu Val Thr Leu Pro Leu Ile Ser Ser Leu Gln Val Glu Glu
545                 550                 555
```

( 2 ) INFORMATION FOR SEQ ID NO:4:

( i ) SEQUENCE CHARACTERISTICS:

( A ) LENGTH: 3632 base pairs ( B ) TYPE: nucleic acid ( C ) STRANDEDNESS: single ( D ) TOPOLOGY: linear ( i i ) MOLECULE TYPE: cDNA ( i x ) FEATURE:
( A ) NAME/KEY: CDS
( B ) LOCATION: 62..1798

( i x ) FEATURE:
( A ) NAME/KEY: mat_peptide
( B ) LOCATION: 125..1798

( x i ) SEQUENCE DESCRIPTION: SEQ ID NO:4:

```
AAAGAGCTGG AGGCGCGCAG GCCGGCTCCG CTCCGGCCCC GGACGATGCG GCGCGCCCAG     60

G ATG CTG CCG TGC CTC GTA GTG CTG CTG GCG GCG CTC CTC AGC CTC        106
  Met Leu Pro Cys Leu Val Val Leu Leu Ala Ala Leu Leu Ser Leu
  -21 -20                 -15                 -10

CGT CTT GGC TCA GAC GCT CAT GGG ACA GAG CTG CCC AGC CCT CCG TCT      154
Arg Leu Gly Ser Asp Ala His Gly Thr Glu Leu Pro Ser Pro Pro Ser
     -5                  1               5                  10

GTG TGG TTT GAA GCA GAA TTT TTC CAC CAC ATC CTC CAC TGG ACA CCC      202
Val Trp Phe Glu Ala Glu Phe Phe His His Ile Leu His Trp Thr Pro
                15                  20                  25

ATC CCA AAT CAG TCT GAA AGT ACC TGC TAT GAA GTG GCG CTC CTG AGG      250
Ile Pro Asn Gln Ser Glu Ser Thr Cys Tyr Glu Val Ala Leu Leu Arg
            30                  35                  40

TAT GGA ATA GAG TCC TGG AAC TCC ATC TCC AAC TGT AGC CAG ACC CTG      298
Tyr Gly Ile Glu Ser Trp Asn Ser Ile Ser Asn Cys Ser Gln Thr Leu
        45                  50                  55

TCC TAT GAC CTT ACC GCA GTG ACC TTG GAC CTG TAC CAC AGC AAT GGC      346
Ser Tyr Asp Leu Thr Ala Val Thr Leu Asp Leu Tyr His Ser Asn Gly
    60                  65                  70

TAC CGG GCC AGA GTG CGG GCT GTG GAC GGC AGC CGG CAC TCC AAC TGG      394
Tyr Arg Ala Arg Val Arg Ala Val Asp Gly Ser Arg His Ser Asn Trp
 75                  80                  85                  90

ACC GTC ACC AAC ACC CGC TTC TCT GTG GAT GAA GTG ACT CTG ACA GTT      442
Thr Val Thr Asn Thr Arg Phe Ser Val Asp Glu Val Thr Leu Thr Val
                95                 100                 105

GGC AGT GTG AAC CTA GAG ATC CAC AAT GGC TTC ATC CTC GGG AAG ATT      490
Gly Ser Val Asn Leu Glu Ile His Asn Gly Phe Ile Leu Gly Lys Ile
           110                 115                 120

CAG CTA CCC AGG CCC AAG ATG GCC CCC GCG AAT GAC ACA TAT GAA AGC      538
Gln Leu Pro Arg Pro Lys Met Ala Pro Ala Asn Asp Thr Tyr Glu Ser
        125                 130                 135

ATC TTC AGT CAC TTC CGA GAG TAT GAG ATT GCC ATT CGC AAG GTG CCG      586
Ile Phe Ser His Phe Arg Glu Tyr Glu Ile Ala Ile Arg Lys Val Pro
    140                 145                 150

GGA AAC TTC ACG TTC ACA CAC AAG AAA GTA AAA CAT GAA AAC TTC AGC      634
Gly Asn Phe Thr Phe Thr His Lys Lys Val Lys His Glu Asn Phe Ser
155                 160                 165                 170

CTC CTA ACC TCT GGA GAA GTG GGA GAG TTC TGT GTC CAG GTG AAA CCA      682
Leu Leu Thr Ser Gly Glu Val Gly Glu Phe Cys Val Gln Val Lys Pro
                175                 180                 185

TCT GTC GCT TCC CGA AGT AAC AAG GGG ATG TGG TCT AAA GAG GAG TGC      730
Ser Val Ala Ser Arg Ser Asn Lys Gly Met Trp Ser Lys Glu Glu Cys
            190                 195                 200

ATC TCC CTC ACC AGG CAG TAT TTC ACC GTG ACC AAC GTC ATC ATC TTC      778
Ile Ser Leu Thr Arg Gln Tyr Phe Thr Val Thr Asn Val Ile Ile Phe
        205                 210                 215

TTT GCC TTT GTC CTG CTG CTC TCC GGA GCC CTC GCC TAC TGC CTG GCC      826
Phe Ala Phe Val Leu Leu Leu Ser Gly Ala Leu Ala Tyr Cys Leu Ala
    220                 225                 230

CTC CAG CTG TAT GTG CGG CGC CGA AAG AAG CTA CCC AGT GTC CTG CTC      874
```

-continued

Leu Gln Leu Tyr Val Arg Arg Arg Lys Lys Leu Pro Ser Val Leu Leu
235 240 245 250

TTC AAG AAG CCC AGC CCC TTC ATC TTC ATC AGC CAG CGT CCC TCC CCA 922
Phe Lys Lys Pro Ser Pro Phe Ile Phe Ile Ser Gln Arg Pro Ser Pro
255 260 265

GAG ACC CAA GAC ACC ATC CAC CCG CTT GAT GAG GAG GCC TTT TTG AAG 970
Glu Thr Gln Asp Thr Ile His Pro Leu Asp Glu Glu Ala Phe Leu Lys
270 275 280

GTG TCC CCA GAG CTG AAG AAC TTG GAC CTG CAC GGC AGC ACA GAC AGT 1018
Val Ser Pro Glu Leu Lys Asn Leu Asp Leu His Gly Ser Thr Asp Ser
285 290 295

GGC TTT GGC AGC ACC AAG CCA TCC CTG CAG ACT GAA GAG CCC CAG TTC 1066
Gly Phe Gly Ser Thr Lys Pro Ser Leu Gln Thr Glu Glu Pro Gln Phe
300 305 310

CTC CTC CCT GAC CCT CAC CCC CAG GCT GAC AGA ACG CTG GGA AAC GGG 1114
Leu Leu Pro Asp Pro His Pro Gln Ala Asp Arg Thr Leu Gly Asn Gly
315 320 325 330

GAG CCC CCT GTG CTG GGG GAC AGC TGC AGT AGT GGC AGC AGC AAT AGC 1162
Glu Pro Pro Val Leu Gly Asp Ser Cys Ser Ser Gly Ser Ser Asn Ser
335 340 345

ACA GAC AGC GGG ATC TGC CTG CAG GAG CCC AGC CTG AGC CCC AGC ACA 1210
Thr Asp Ser Gly Ile Cys Leu Gln Glu Pro Ser Leu Ser Pro Ser Thr
350 355 360

GGG CCC ACC TGG GAG CAA CAG GTG GGG AGC AAC AGC AGG GGC CAG GAT 1258
Gly Pro Thr Trp Glu Gln Gln Val Gly Ser Asn Ser Arg Gly Gln Asp
365 370 375

GAC AGT GGC ATT GAC TTA GTT CAA AAC TCT GAG GGC CGG GCT GGG GAC 1306
Asp Ser Gly Ile Asp Leu Val Gln Asn Ser Glu Gly Arg Ala Gly Asp
380 385 390

ACA CAG GGT GGC TCG GCC TTG GGC CAC CAC AGT CCC CCG GAG CCT GAG 1354
Thr Gln Gly Gly Ser Ala Leu Gly His His Ser Pro Pro Glu Pro Glu
395 400 405 410

GTG CCT GGG GAA GAA GAC CCA GCT GCT GTG GCA TTC CAG GGT TAC CTG 1402
Val Pro Gly Glu Glu Asp Pro Ala Ala Val Ala Phe Gln Gly Tyr Leu
415 420 425

AGG CAG ACC AGA TGT GCT GAA GAG AAG GCA ACC AAG ACA GGC TGC CTG 1450
Arg Gln Thr Arg Cys Ala Glu Glu Lys Ala Thr Lys Thr Gly Cys Leu
430 435 440

GAG GAA GAA TCG CCC TTG ACA GAT GGC CTT GGC CCC AAA TTC GGG AGA 1498
Glu Glu Glu Ser Pro Leu Thr Asp Gly Leu Gly Pro Lys Phe Gly Arg
445 450 455

TGC CTG GTT GAT GAG GCA GGC TTG CAT CCA CCA GCC CTG GCC AAG GGC 1546
Cys Leu Val Asp Glu Ala Gly Leu His Pro Pro Ala Leu Ala Lys Gly
460 465 470

TAT TTG AAA CAG GAT CCT CTA GAA ATG ACT CTG GCT TCC TCA GGG GCC 1594
Tyr Leu Lys Gln Asp Pro Leu Glu Met Thr Leu Ala Ser Ser Gly Ala
475 480 485 490

CCA ACG GGA CAG TGG AAC CAG CCC ACT GAG GAA TGG TCA CTC CTG GCC 1642
Pro Thr Gly Gln Trp Asn Gln Pro Thr Glu Glu Trp Ser Leu Leu Ala
495 500 505

TTG AGC AGC TGC AGT GAC CTG GGA ATA TCT GAC TGG AGC TTT GCC CAT 1690
Leu Ser Ser Cys Ser Asp Leu Gly Ile Ser Asp Trp Ser Phe Ala His
510 515 520

GAC CTT GCC CCT CTA GGC TGT GTG GCA GCC CCA GGT GGT CTC CTG GGC 1738
Asp Leu Ala Pro Leu Gly Cys Val Ala Ala Pro Gly Gly Leu Leu Gly
525 530 535

AGC TTT AAC TCA GAC CTG GTC ACC CTG CCC CTC ATC TCT AGC CTG CAG 1786
Ser Phe Asn Ser Asp Leu Val Thr Leu Pro Leu Ile Ser Ser Leu Gln
540 545 550

TCA AGT GAG TGACTCGGGC TGAGAGGCTG CTTTTGATTT TAGCCATGCC 1835

-continued

Ser Ser Glu
555

TGCTCCTCTG CCTGGACCAG GAGGAGGGCC CTGGGGCAGA AGTTAGGCAC GAGGCAGTCT 1895

GGGCACTTTT CTGCAAGTCC ACTGGGGCTG GCCCAGCCAG GCTGCAGGGC TGGTCAGGGT 1955

GTCTGGGGCA GGAGGAGGCC AACTCACTGA ACTAGTGCAG GGTATGTGGG TGGCACTGAC 2015

CTGTTCTGTT GACTGGGGCC CTGCAGACTC TGGCAGAGCT GAGAAGGGCA GGGACCTTCT 2075

CCCTCCTAGG AACTCTTTCC TGTATCATAA AGGATTATTT GCTCAGGGGA ACCATGGGGC 2135

TTTCTGGAGT TGTGGTGAGG CCACCAGGCT GAAGTCAGCT CAGACCCAGA CCTCCCTGCT 2195

TAGGCCACTC GAGCATCAGA GCTTCCAGCA GGAGGAAGGG CTGTAGGAAT GGAAGCTTCA 2255

GGGCCTTGCT GCTGGGGTCA TTTTTAGGGG AAAAAGGAGG ATATGATGGT CACATGGGGA 2315

ACCTCCCCTC ATCGGGCCTC TGGGGCAGGA AGCTTGTCAC TGGAAGATCT TAAGGTATAT 2375

ATTTTCTGGA CACTCAAACA CATCATAATG GATTCACTGA GGGGAGACAA AGGGAGCCGA 2435

GACCCTGGAT GGGGCTTCCA GCTCAGAACC CATCCCTCTG GTGGGTACCT CTGGCACCCA 2495

TCTGCAAATA TCTCCCTCTC TCCAACAAAT GGAGTAGCAT CCCCCTGGGG CACTTGCTGA 2555

GGCCAAGCCA CTCACATCCT CACTTTGCTG CCCCACCATC TTGCTGACAA CTTCCAGAGA 2615

AGCCATGGTT TTTTGTATTG GTCATAACTC AGCCCTTTGG GCGGCCTCTG GGCTTGGGCA 2675

CCAGCTCATG CCAGCCCCAG AGGGTCAGGG TTGGAGGCCT GTGCTTGTGT TTGCTGCTAA 2735

TGTCCAGCTA CAGACCCAGA GGATAAGCCA CTGGGCACTG GGCTGGGGTC CCTGCCTTGT 2795

TGGTGTTCAG CTGTGTGATT TTGGACTAGC CACTTGTCAG AGGGCCTCAA TCTCCCATCT 2855

GTGAAATAAG GACTCCACCT TTAGGGGACC CTCCATGTTT GCTGGGTATT AGCCAAGCTG 2915

GTCCTGGGAG AATGCAGATA CTGTCCGTGG ACTACCAAGC TGGCTTGTTT CTTATGCCAG 2975

AGGCTAACAG ATCCAATGGG AGTCCATGGT GTCATGCCAA GACAGTATCA GACACAGCCC 3035

CAGAAGGGGG CATTATGGGC CCTGCCTCCC CATAGGCCAT TTGGACTCTG CCTTCAAACA 3095

AAGGCAGTTC AGTCCACAGG CATGGAAGCT GTGAGGGGAC AGGCCTGTGC GTGCCATCCA 3155

GAGTCATCTC AGCCCTGCCT TTCTCTGGAG CATTCTGAAA ACAGATATTC TGGCCCAGGG 3215

AATCCAGCCA TGACCCCCAC CCCTCTGCCA AAGTACTCTT AGGTGCCAGT CTGGTAACTG 3275

AACTCCCTCT GGAGGCAGGC TTGAGGGAGG ATTCCTCAGG GTTCCCTTGA AAGCTTTATT 3335

TATTTATTTT GTTCATTTAT TTATTGGAGA GGCAGCATTG CACAGTGAAA GAATTCTGGA 3395

TATCTCAGGA GCCCCGAAAT TCTAGCTCTG ACTTTGCTGT TTCCAGTGGT ATGACCTTGG 3455

AGAAGTCACT TATCCTCTTG GAGCCTCAGT TTCCTCATCT GCAGAATAAT GACTGACTTG 3515

TCTAATTCAT AGGGATGTGA GGTTCTGCTG AGGAAATGGG TATGAATGTG CCTTGAACAC 3575

AAAGCTCTGT CAATAAGTGA TACATGTTTT TTATTCCAAT AAATTGTCAA GACCACA 3632

( 2 ) INFORMATION FOR SEQ ID NO:5:

( i ) SEQUENCE CHARACTERISTICS:
( A ) LENGTH: 578 amino acids
( B ) TYPE: amino acid
( D ) TOPOLOGY: linear ( i i ) MOLECULE TYPE: protein ( x i ) SEQUENCE DESCRIPTION: SEQ ID NO:5:

Met Leu Pro Cys Leu Val Val Leu Leu Ala Ala Leu Leu Ser Leu Arg
-21 -20 -15 -10

Leu Gly Ser Asp Ala His Gly Thr Glu Leu Pro Ser Pro Pro Ser Val
-5 1 5 10

-continued

```
Trp Phe Glu Ala Glu Phe Phe His His Ile Leu His Trp Thr Pro Ile
            15                  20                  25

Pro Asn Gln Ser Glu Ser Thr Cys Tyr Glu Val Ala Leu Leu Arg Tyr
        30                  35                  40

Gly Ile Glu Ser Trp Asn Ser Ile Ser Asn Cys Ser Gln Thr Leu Ser
    45                  50                  55

Tyr Asp Leu Thr Ala Val Thr Leu Asp Leu Tyr His Ser Asn Gly Tyr
60                  65                  70                  75

Arg Ala Arg Val Arg Ala Val Asp Gly Ser Arg His Ser Asn Trp Thr
                80                  85                  90

Val Thr Asn Thr Arg Phe Ser Val Asp Glu Val Thr Leu Thr Val Gly
            95                  100                 105

Ser Val Asn Leu Glu Ile His Asn Gly Phe Ile Leu Gly Lys Ile Gln
        110                 115                 120

Leu Pro Arg Pro Lys Met Ala Pro Ala Asn Asp Thr Tyr Glu Ser Ile
    125                 130                 135

Phe Ser His Phe Arg Glu Tyr Glu Ile Ala Ile Arg Lys Val Pro Gly
140                 145                 150                 155

Asn Phe Thr Phe Thr His Lys Lys Val Lys His Glu Asn Phe Ser Leu
                160                 165                 170

Leu Thr Ser Gly Glu Val Gly Glu Phe Cys Val Gln Val Lys Pro Ser
            175                 180                 185

Val Ala Ser Arg Ser Asn Lys Gly Met Trp Ser Lys Glu Glu Cys Ile
        190                 195                 200

Ser Leu Thr Arg Gln Tyr Phe Thr Val Thr Asn Val Ile Ile Phe Phe
    205                 210                 215

Ala Phe Val Leu Leu Leu Ser Gly Ala Leu Ala Tyr Cys Leu Ala Leu
220                 225                 230                 235

Gln Leu Tyr Val Arg Arg Arg Lys Lys Leu Pro Ser Val Leu Leu Phe
                240                 245                 250

Lys Lys Pro Ser Pro Phe Ile Phe Ile Ser Gln Arg Pro Ser Pro Glu
            255                 260                 265

Thr Gln Asp Thr Ile His Pro Leu Asp Glu Glu Ala Phe Leu Lys Val
        270                 275                 280

Ser Pro Glu Leu Lys Asn Leu Asp Leu His Gly Ser Thr Asp Ser Gly
    285                 290                 295

Phe Gly Ser Thr Lys Pro Ser Leu Gln Thr Glu Glu Pro Gln Phe Leu
300                 305                 310                 315

Leu Pro Asp Pro His Pro Gln Ala Asp Arg Thr Leu Gly Asn Gly Glu
                320                 325                 330

Pro Pro Val Leu Gly Asp Ser Cys Ser Ser Gly Ser Ser Asn Ser Thr
            335                 340                 345

Asp Ser Gly Ile Cys Leu Gln Glu Pro Ser Leu Ser Pro Ser Thr Gly
        350                 355                 360

Pro Thr Trp Glu Gln Gln Val Gly Ser Asn Ser Arg Gly Gln Asp Asp
    365                 370                 375

Ser Gly Ile Asp Leu Val Gln Asn Ser Glu Gly Arg Ala Gly Asp Thr
380                 385                 390                 395

Gln Gly Gly Ser Ala Leu Gly His His Ser Pro Pro Glu Pro Glu Val
                400                 405                 410

Pro Gly Glu Glu Asp Pro Ala Ala Val Ala Phe Gln Gly Tyr Leu Arg
            415                 420                 425

Gln Thr Arg Cys Ala Glu Glu Lys Ala Thr Lys Thr Gly Cys Leu Glu
```

430 435 440

Glu Glu Ser Pro Leu Thr Asp Gly Leu Gly Pro Lys Phe Gly Arg Cys
445 450 455

Leu Val Asp Glu Ala Gly Leu His Pro Pro Ala Leu Ala Lys Gly Tyr
460 465 470 475

Leu Lys Gln Asp Pro Leu Glu Met Thr Leu Ala Ser Ser Gly Ala Pro
480 485 490

Thr Gly Gln Trp Asn Gln Pro Thr Glu Glu Trp Ser Leu Leu Ala Leu
495 500 505

Ser Ser Cys Ser Asp Leu Gly Ile Ser Asp Trp Ser Phe Ala His Asp
510 515 520

Leu Ala Pro Leu Gly Cys Val Ala Ala Pro Gly Gly Leu Leu Gly Ser
525 530 535

Phe Asn Ser Asp Leu Val Thr Leu Pro Leu Ile Ser Ser Leu Gln Ser
540 545 550 555

Ser Glu ( 2 ) INFORMATION FOR SEQ ID NO:6:

( i ) SEQUENCE CHARACTERISTICS:
( A ) LENGTH: 557 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:6:

His Gly Thr Glu Leu Pro Ser Pro Pro Ser Val Trp Phe Glu Ala Glu
1 5 10 15

Phe Phe His His Ile Leu His Trp Thr Pro Ile Pro Asn Gln Ser Glu
20 25 30

Ser Thr Cys Tyr Glu Val Ala Leu Leu Arg Tyr Gly Ile Glu Ser Trp
35 40 45

Asn Ser Ile Ser Asn Cys Ser Gln Thr Leu Ser Tyr Asp Leu Thr Ala
50 55 60

Val Thr Leu Asp Leu Tyr His Ser Asn Gly Tyr Arg Ala Arg Val Arg
65 70 75 80

Ala Val Asp Gly Ser Arg His Ser Asn Trp Thr Val Thr Asn Thr Arg
85 90 95

Phe Ser Val Asp Glu Val Thr Leu Thr Val Gly Ser Val Asn Leu Glu
100 105 110

Ile His Asn Gly Phe Ile Leu Gly Lys Ile Gln Leu Pro Arg Pro Lys
115 120 125

Met Ala Pro Ala Asn Asp Thr Tyr Glu Ser Ile Phe Ser His Phe Arg
130 135 140

Glu Tyr Glu Ile Ala Ile Arg Lys Val Pro Gly Asn Phe Thr Phe Thr
145 150 155 160

His Lys Lys Val Lys His Glu Asn Phe Ser Leu Leu Thr Ser Gly Glu
165 170 175

Val Gly Glu Phe Cys Val Gln Val Lys Pro Ser Val Ala Ser Arg Ser
180 185 190

Asn Lys Gly Met Trp Ser Lys Glu Glu Cys Ile Ser Leu Thr Arg Gln
195 200 205

Tyr Phe Thr Val Thr Asn Val Ile Ile Phe Phe Ala Phe Val Leu Leu
210 215 220

-continued

Leu Ser Gly Ala Leu Ala Tyr Cys Leu Ala Leu Gln Leu Tyr Val Arg
225 230 235 240

Arg Arg Lys Lys Leu Pro Ser Val Leu Leu Phe Lys Lys Pro Ser Pro
245 250 255

Phe Ile Phe Ile Ser Gln Arg Pro Ser Pro Glu Thr Gln Asp Thr Ile
260 265 270

His Pro Leu Asp Glu Glu Ala Phe Leu Lys Val Ser Pro Glu Leu Lys
275 280 285

Asn Leu Asp Leu His Gly Ser Thr Asp Ser Gly Phe Gly Ser Thr Lys
290 295 300

Pro Ser Leu Gln Thr Glu Glu Pro Gln Phe Leu Leu Pro Asp Pro His
305 310 315 320

Pro Gln Ala Asp Arg Thr Leu Gly Asn Gly Glu Pro Pro Val Leu Gly
325 330 335

Asp Ser Cys Ser Ser Gly Ser Ser Asn Ser Thr Asp Ser Gly Ile Cys
340 345 350

Leu Gln Glu Pro Ser Leu Ser Pro Ser Thr Gly Pro Thr Trp Glu Gln
355 360 365

Gln Val Gly Ser Asn Ser Arg Gly Gln Asp Asp Ser Gly Ile Asp Leu
370 375 380

Val Gln Asn Ser Glu Gly Arg Ala Gly Asp Thr Gln Gly Gly Ser Ala
385 390 395 400

Leu Gly His His Ser Pro Pro Glu Pro Glu Val Pro Gly Glu Glu Asp
405 410 415

Pro Ala Ala Val Ala Phe Gln Gly Tyr Leu Arg Gln Thr Arg Cys Ala
420 425 430

Glu Glu Lys Ala Thr Lys Thr Gly Cys Leu Glu Glu Glu Ser Pro Leu
435 440 445

Thr Asp Gly Leu Gly Pro Lys Phe Gly Arg Cys Leu Val Asp Glu Ala
450 455 460

Gly Leu His Pro Pro Ala Leu Ala Lys Gly Tyr Leu Lys Gln Asp Pro
465 470 475 480

Leu Glu Met Thr Leu Ala Ser Ser Gly Ala Pro Thr Gly Gln Trp Asn
485 490 495

Gln Pro Thr Glu Glu Trp Ser Leu Leu Ala Leu Ser Ser Cys Ser Asp
500 505 510

Leu Gly Ile Ser Asp Trp Ser Phe Ala His Asp Leu Ala Pro Leu Gly
515 520 525

Cys Val Ala Ala Pro Gly Gly Leu Leu Gly Ser Phe Asn Ser Asp Leu
530 535 540

Val Thr Leu Pro Leu Ile Ser Ser Leu Gln Ser Ser Glu
545 550 555

( 2 ) INFORMATION FOR SEQ ID NO:7:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

CCAGTGGTAC ATCCGGCACC CGGGGAAGTT GCC 33

( 2 ) INFORMATION FOR SEQ ID NO:8:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

CGTCCGAAGC GCGGCCGCTC ATCATCACTG GTCCTGATGG GTATATCCAA GCTGCTG 57

( 2 ) INFORMATION FOR SEQ ID NO:9:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

CGTCCGAAGC GCGGCCGCTC ATCATCAAGA TGCATCCTGT GTGTACTTAG GCTGCCC 57

( 2 ) INFORMATION FOR SEQ ID NO:10:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:10:

CGTCCGAAGC GCGGCCGCTC ATCATCATCT GGTCTGTTTC TGGTAGCCCT GGAATGT 57

( 2 ) INFORMATION FOR SEQ ID NO:11:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

CGTCCGAAGC GCGGCCGCTC ATCATCATTC TTCTACCTGC AGGCTGGAGA TCAACGGCAG 60

( 2 ) INFORMATION FOR SEQ ID NO:12:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:12:

CCCGATGCCA TTCACATCGT GGACCTGGAG GTTTTCCC 38

( 2 ) INFORMATION FOR SEQ ID NO:13:

( i ) SEQUENCE CHARACTERISTICS:
( A ) LENGTH: 57 base pairs
( B ) TYPE: nucleic acid
( C ) STRANDEDNESS: single ( D ) TOPOLOGY: linear ( i i ) MOLECULE TYPE: cDNA ( x i ) SEQUENCE DESCRIPTION: SEQ ID NO:13:

CGTCCGAAGC ACATCGTGTC TCCAGGGCAG CCTAAGTACA CACAGGATGC ATCTGCC 57

( 2 ) INFORMATION FOR SEQ ID NO:14:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:14:

CGTCCGAAGC ACATCGTGGA GGAGAAAGAC CAAGTCATGG TGACATTCCA GGGCTACCAG 60

( 2 ) INFORMATION FOR SEQ ID NO:15:

( i ) SEQUENCE CHARACTERISTICS:
( A ) LENGTH: 60 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:15:

CGTCCGAAGC ACATCGTGGG GGTACACCTG CAGGATGATT TGGCTTGGCC TCCACCAGCT 60

( 2 ) INFORMATION FOR SEQ ID NO:16:

( i ) SEQUENCE CHARACTERISTICS:
( A ) LENGTH: 57 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:16:

CGTCCGAAGC GCGGCCGCTC ATCATCAAGA CTCCTGTTTC AAATAACCTG CGGCCAG 57

MAMMALIAN INTERLEUKIN-10 (IL-10) SUPER-ACTIVATING RECEPTORS; AND VARIANTS

This application hereby incorporates by reference each of the following patent applications: U.S. Ser. No. 08/110,683, filed on Aug. 23, 1993, which is a continuation of commonly assigned then patent application U.S. Ser. No. 08/011,066, filed on Jan. 29, 1993, now abandoned, which is a continuation of then patent application U.S. Ser. No. 07/989,792, filed on Dec. 10, 1992, now abandoned.

FIELD OF THE INVENTION

The present invention relates generally to nucleic acids and polypeptides characteristic of variants of receptors for mammalian interleukin-10 (IL-10). These variants display at least 5 fold greater response to ligand binding than a wild-type receptor. More particularly, this invention embraces use of variant receptors in preparing reagents useful for diagnosing or treating various IL-10 or receptor-related medical conditions.

BACKGROUND OF THE INVENTION

The proliferation, differentiation, and effector function of immune cells are regulated by a complex network of interactions. Although many of these processes involve cell-cell contact, most are mediated wholly or in part by the cytokines, a family of proteins secreted by activated hemopoietic cells. See Ho, et al. (1994) *Ther. Immunol.* 1:173–185. Most cytokines have more than one biological activity. The activity which is regarded as the most important likely depends on the local context in which the cytokine is produced.

As soluble intercellular messenger molecules, the cytokines typically bind to cellular receptors, e.g., cell surface receptors. Receptor molecules have been identified and isolated for G-CSF, GM-CSF, EPO, TNF, IFN-γ, IL-2, IL-3, IL-4, IL-5, IL-6, and IL-7. See Gearing, et al. (1989) *EMBO J,* 8:3667–3676 (low affinity α chain of the human GM-CSF receptor); Itoh, et al. (1990) *Science* 247:324–327 (low affinity α chain of a mouse IL-3 receptor); Hayashida, et al. (1990) *Proc. Nat'l. Acad. Sci.* 87:9655–9659 (a β chain of a human GM-CSF receptor); and Tavernier, et al. (1991) *Cell* 66:1175–84 (IL-5 receptor, α and β chains). Many of these receptors have two chains, both of which are members of the hemopoietic receptor superfamily. In such cases, typically one chain, designated the α chain, can bind its ligand with low affinity which may or may not result in transduction to the cell of a signal. Following the binding of a ligand to the α chain, another chain, designated the β chain, is recruited and associates with the α chain. This interaction confers higher affinity binding of the heterodimeric receptor to the cytokine. See Miyajima, et al. (1992) *Ann. Rev. Immunol.* 295–331. The β chain by itself usually lacks significant ligand binding affinity. The dimeric form of receptor is capable of transducing a signal into the cell as a consequence of ligand, e.g., cytokine, binding. Additional subunits or accessory proteins may also be associated with the receptors.

The various components of the earlier identified receptors appear to share properties useful in defining a receptor superfamily of related proteins. See Bazan (1990) *Immunology Today* 11:350–354; and Bazan (1990) Proc. Nat'l Acad. Sci. USA 87:6934–6938. However, the structure and mechanism of action of a receptor for a mammalian interleukin-10 (IL-10) could not be predicted with reliability based merely upon speculated similarity to receptors for other cytokines.

A cytokine synthesis inhibitory factor (CSIF) activity led to assays which allowed the isolation of a cytokine designated interleukin-10 (IL-10). See Fiorentino, et al. (1989) *J. Exp. Med.* 170:2081–2095; and Mosmann, et al. (1991) Immunol. Today 12:A49–A53. Both mouse and human counterparts have been isolated. See Moore, et al. (1990) *Science* 248:1230–1234; and Vieira, et al. (1991) *Proc. Nat'l Acad. Sci. USA* 88:1172–1176. A human viral analog, known as either vIL-10 or BCRF1, has been described which shares many characteristic activities of the natural human form. See Hsu, et al. (1990) *Science* 250:830–832. Another viral homologue has been described from an equine herpes virus. See Rode, et al. (1993) *Virus Genes* 7:111–117.

IL-10 inhibits cytokine synthesis by activated T cells, stimulates growth for thymocytes and mast cells, induces class II MHC expression, and sustains viability in culture of small dense resting mouse B cells.

As with other cytokines, the biological effects of IL-10 are mediated through cell-surface receptors. Human and mouse receptor subunits for IL-10 have been identified and found to be members of the interferon receptor (IFNR)-like subgroup of the cytokine receptor family. See Tan, et al. (1993) *J. Biol. Chem.* 268:21053–21059; Ho, et al. (1993) *Proc. Natl. Acad. Sci.* 90:11267–11271; and Liu, et al., (1994) *J. Immunol,* 152:1821–1829.

The relationship between the structure and the function of the IL-10 receptor remains poorly understood. As such, sensitive assays to detect ligands, antagonists, and/or agonists will be increasingly useful. The creation of variant receptors which are highly responsive to ligand binding, i.e., super-activating receptors, will provide means for creating such assays and ability to detect small quantities of ligand.

Understanding signal transduction and other intracellular signaling pathways that are activated after ligand binding is important for elucidating the mechanisms that control cellular growth, differentiation, and activation. Cellular signaling is still being investigated, but knowledge of these pathways will provide information to create agonists or antagonists of cell growth and development.

Thus, a need exists for Creating mutants of the IL-10 receptor exhibiting increased sensitivity to the ligand. These will also be useful to characterize regions which mediate different responses of ligand binding. The present invention provides these and the means of preparing many useful reagents.

SUMMARY OF THE INVENTION

The present invention is based in part on the surprising result that deletion mutants of a wild-type mammalian IL-10 receptor can be made which are more sensitive to a ligand, i.e., providing a higher proliferative response upon the presence of lower amounts of ligand, than the wild-type counterpart. A mouse super-activating IL-10 receptor is exemplified, though corresponding embodiments in other species will be found by similar methods or based on other properties derived therefrom.

The present invention provides super-activating receptor proteins which are deletion mutants of wild-type proteins. The wild-type proteins have sequences, e.g., of SEQ ID NO: 3 or 6. In mouse receptor embodiments, deletions in the membrane proximal region of the cytoplasmic domain can correspond to Asp282 to Asn389, inclusive; Asp282 to Pro414, inclusive; Asp282 to Leu458, inclusive; Asp276 to Thr375 inclusive; Asp 276 to Pro394 inclusive; or Asp276 and Ala435 inclusive of the mature mouse IL-10 polypeptide of SEQ ID NO: 3. The super-activating receptor will have a higher sensitivity to a ligand, which is assayed, e.g., by proliferative response. In various embodiments, the super-activating receptor will ordinarily be at least 5-fold, more ordinarily be at least about 10-fold, preferably at least about 20-fold, and most preferably at least about 50-fold more sensitive than the wild-type counterpart.

The present invention also embraces nucleic acids encoding super-activating mammalian IL-10 receptors from other species. In preferred embodiments, the nucleic acid is deoxyribonucleic acid. Other embodiments include expression vectors expressing DNA encoding a super-activating receptor. The invention also embraces host cells which are mammalian, including mouse cells, preferably Ba/F3 cells.

The invention also encompasses a method of testing a sample for the presence of a ligand by contacting a cell expressing a super-activating receptor with the sample. The cell can be a mammalian cell, including a mouse cell, preferably a Ba/F3 cell.

The invention also provides useful reagents in a kit as a means for detecting the presence of a ligand in a sample. The kit will be comprised of, e.g., a nucleic acid suitable for transfection into a cell, or the super-activating protein expressed on a cell, preferably a mammalian cell.

DETAILED DESCRIPTION OF THE PREFERRED EMBODIMENTS

CONTENTS

Figure 1:
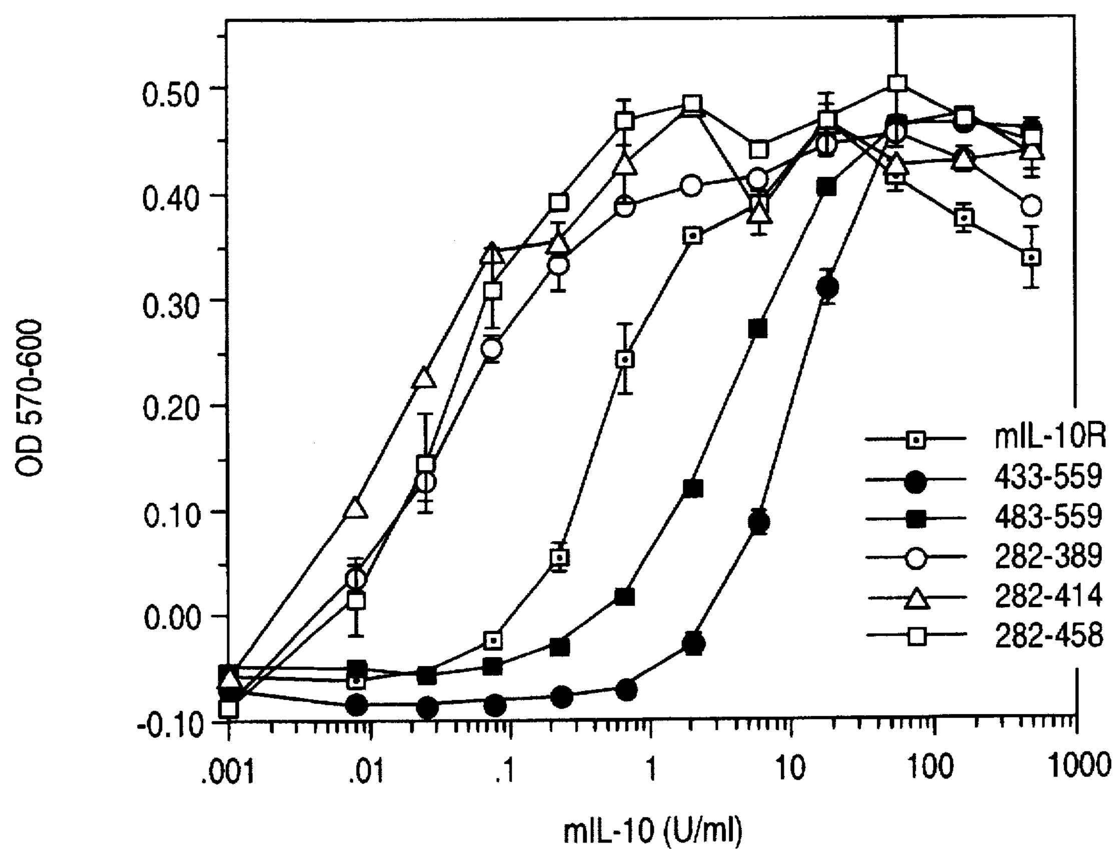
FIG. 1 illustrates the responses of Ba/F3 cells expressing wild-type mIL-10R and cytoplasmic domain mutants.
Figure 2:
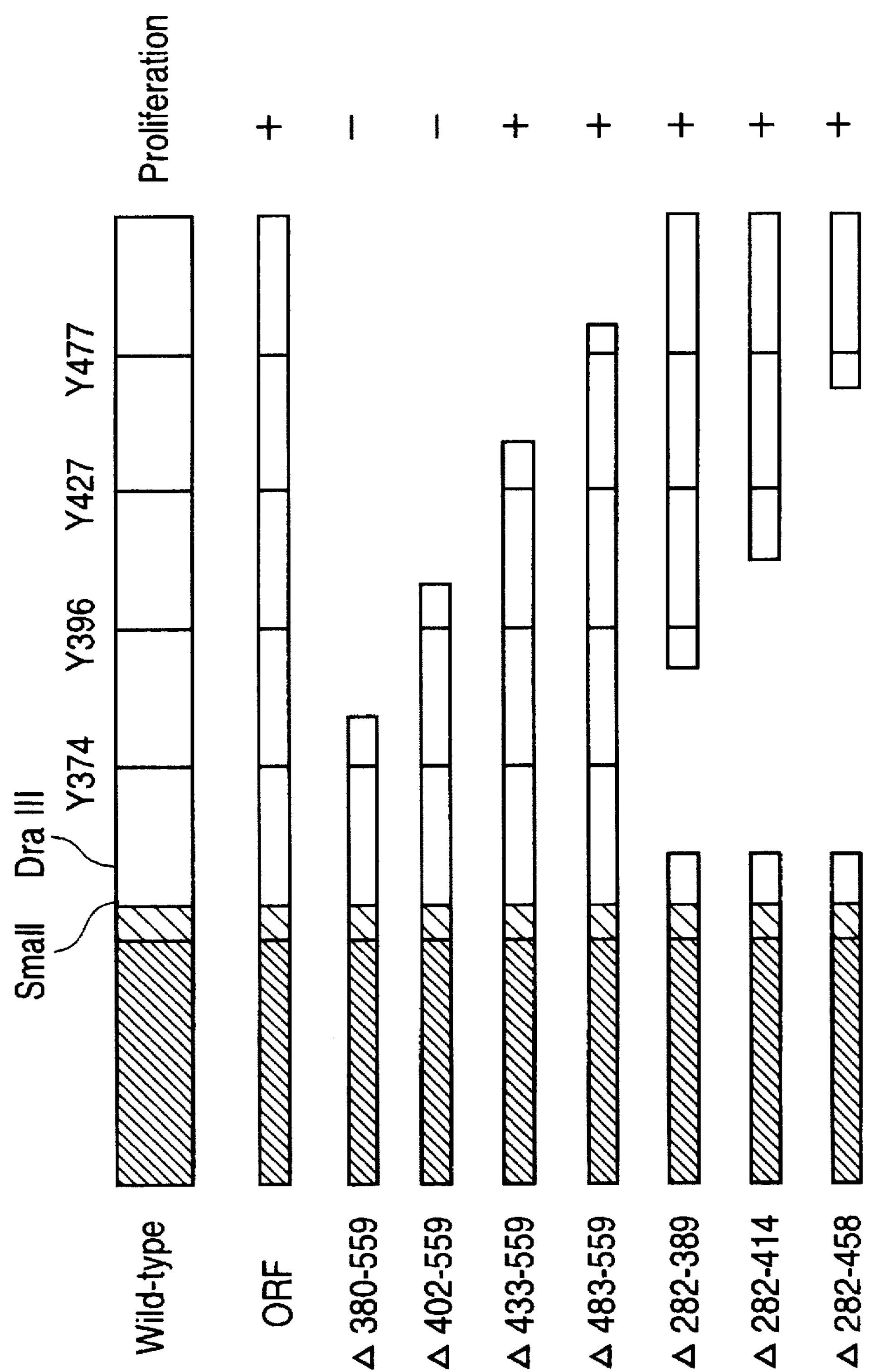
FIG. 2 is a schematic diagram of cytoplasmic domain deletion mutants of mouse IL-10 receptor (mIL-10R). Abilities of each mutant to mediate proliferative responses are indicated by "+" and "–" in the column on the right. Narrowly hatched bar extracellular domain; stippled bar: transmembrane domain.
Figure 3A:
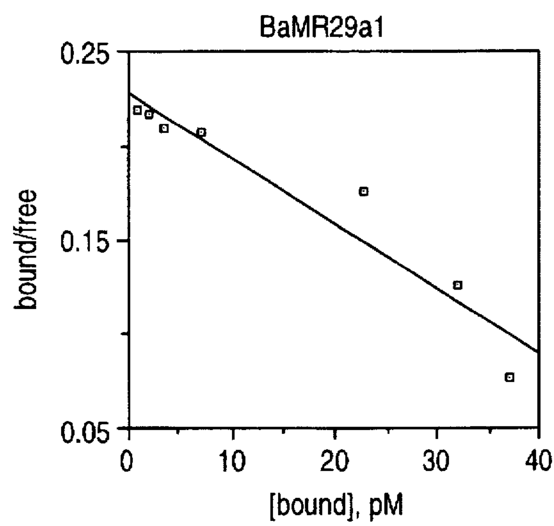
FIGS. 3A–3C show the binding of $^{125}$I-hIL-10 to cells expressing wild-type, Δ282-414, and Δ483-559 mIL-10R. The data are presented. as Scatchard plots; calculated values of Kd and IL-10R number were: 280 pM and 7700 IL-10R/cell (BaMR29al); 670 pM and 22000 IL-10R/cell (Δ282-414); 540 pM and 25000 IL-10R/cell (Δ483-559).
Figure 3B:
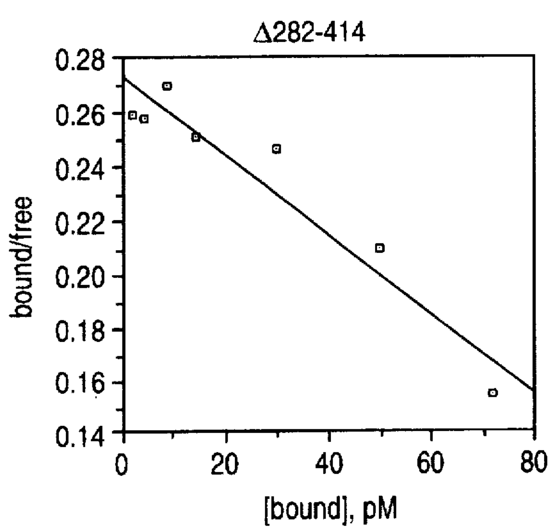
Figure 3C:
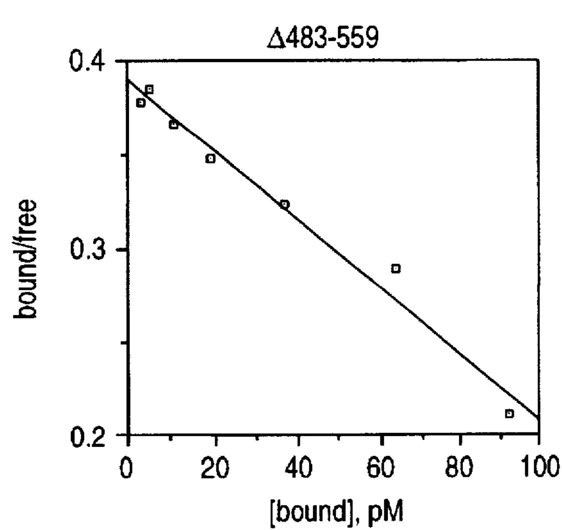
Figure 4:
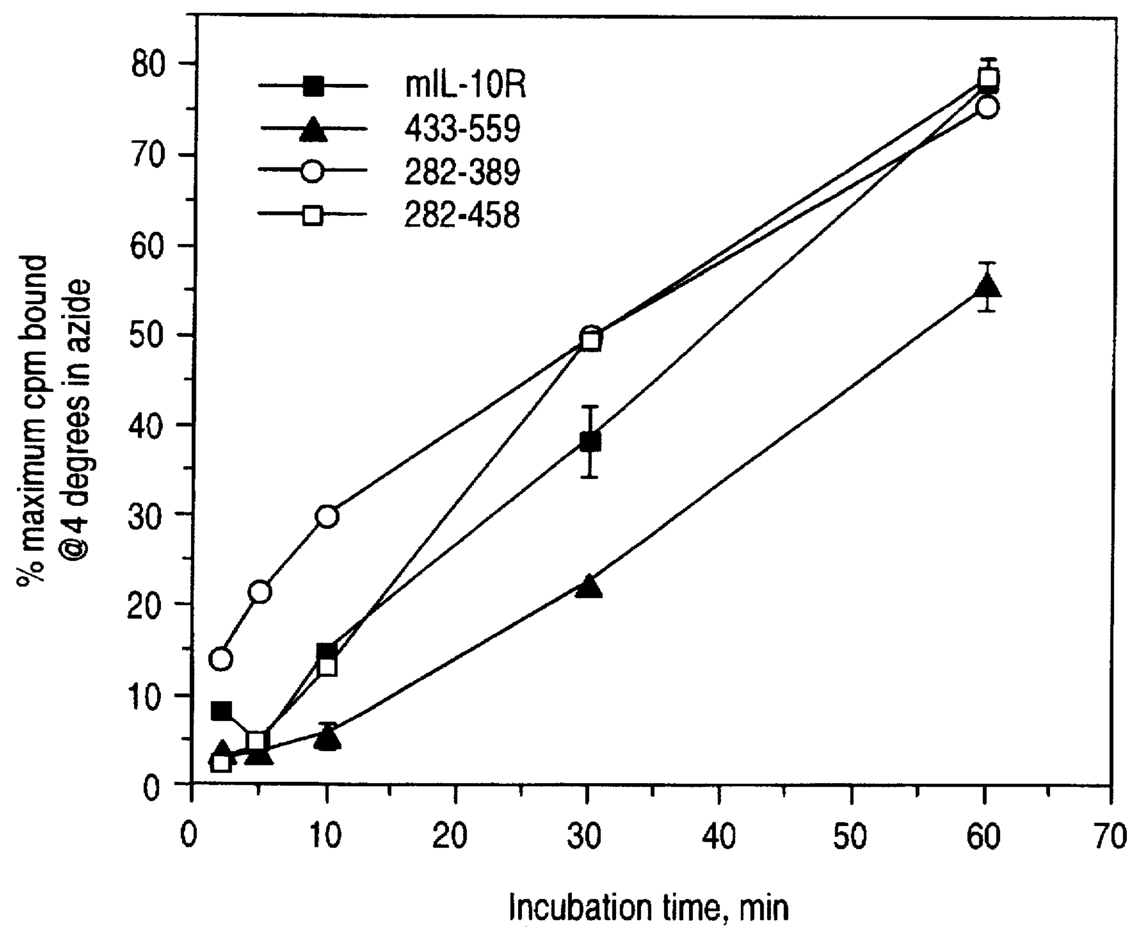
FIG. 4 illustrates the internalization of $^{125}$I-hIL-10 by Ba/F3 cells expressing wild-type and mutant IL-10R. $^{125}$I-hIL-10 internalized after the indicated time at 37° C. is depicted as percent of the total amount bound to the same cells at 4° C. in the presence of azide in 90 min.
Figure 5:
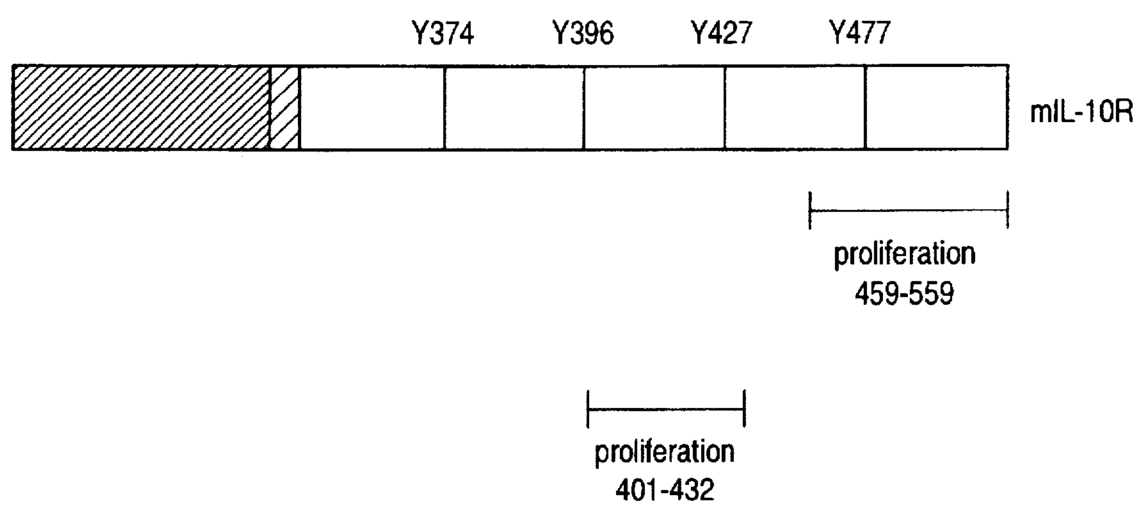
FIG. 5 is a schematic drawing of the functional regions of the mIL-10R cytoplasmic domain.

I. General
II. Receptor Variants
III. Nucleic Acids
IV. Making Receptor
V. Receptor Isolation
VI. Receptor Analogs
VII. Antibodies
VIII. Other Uses of Receptors
IX. Ligands: Agonists and Antagonists
X. Kits
XI. Therapeutic Applications
XII. Additional Receptor Subunits I. General The present invention relates to super-activating mouse IL-10 receptor (mIL-10R) proteins and nucleic acids. Super-activating receptors from other mammals, e.g., human, rat, pig, sheep, goat, etc., are also contemplated.

Ba/F3 cells expressing recombinant IL-10R (BaF-mIL-10R) exhibit a proliferative response to IL-10, whereas the parent Ba/F3 cells do not. See Ho, et al. (1993) *Proc. Natl. Acad. Sci. USA* 90:11267–11271; Liu, et al. (1994) *J. Immunol.* 152:1821–1829; U.S. Ser. No. 08/110,683; U.S. Ser. No. 08/011,066; and U.S. Ser. No. 07/989,792. Both mIL-10 and hIL-10 stimulate BaF-mIL-10R (BaMR29al) cells with similar specific activities of 0.5-1×10$^7$ unit/mg, similar to that observed for the macrophage deactivating factor/CSIF activity of IL-10. See Fiorentino, et al. (1989) *J. Exp. Med.* 170:2081–2095; Ho, et al. (1994) *Therapeutic Immunology* 1:173–185; and Moore, et al. (1993) *Ann. Rev. Immunol.* 11:165–190. See also U.S. Ser. No. 08/110,683, which is incorporated herein by reference.

Mutant mIL-10R containing various deletions of the cytoplasmic domain were prepared and stably expressed in Ba/F3 cells, along with individual tyrosine to phenylalanine (Y→F) mutations of the four tyrosines (Y374F, Y396F, Y427F, and Y477F) in the cytoplasmic domain of the mature mouse IL-10R polypeptide of SEQ ID NO: 3. See Ho, et al. (1993) *Proc. Natl. Acad. Sci. USA* 90:11267–11271. Two independent DNA clone isolates and their stable transfectants were characterized for each mutant. Ba/F3 transfectants stably expressing mutant IL-10R were tested for induction of proliferation by IL-10.

Proliferative responses mediated by many mIL-10R mutants reproducibly differ in sensitivity to IL-10, but the magnitudes (plateau levels) of the responses are all similar. In view of IL-10-induced proliferation observed with deletions of the mature mIL-10R from amino acid 433-559 (Δ433-559) and Δ483-559 of the mIL-10R, it was inferred that the regions Ser401-Arg432 and Gly459-Glu559 are important in mediating the proliferative response to IL-10. None of the Y→F mutants were detectably altered in their ability to stimulate proliferation.

Ba/F3 transfectants expressing membrane-proximal deletion mutants, e.g., Δ282-389, Δ282-414, and Δ282-458, display a striking and unexpected property of a 1.5–2 log greater proliferative response to IL-10 compared to wild-type mIL-10R and are thus termed "super-activating" mutants. This property is not due to a significantly increased mIL-10R expression level or binding affinity for IL-10, since these mutant mIL-10R exhibit ligand binding properties similar to both a non-super-activating mutant (Δ483-559) and wild-type mIL-10R. In fact, Kd values for the mutant mIL-10R (400–600 pM) are somewhat higher than the wild type. See Ho, et al. (1993) *Proc. Natl. Acad. Sci. USA* 90:11267–11271; Tan, et al. (1993) J. Biol. Chem. 268:21053–21059; U.S. Ser. No. 08/110,683; U.S. Ser. No. 08/011,066; and U.S. Ser. No. 07/989,792. Super-activation is also not due to impaired mIL-10R internalization, since mIL-10R Δ282-389 and Δ282-458 internalize $^{125}$I-hIL-10 at least as proficiently as wild-type mIL-10R, and actually better than the non-super-activating Δ433-559 mutant.

The super-activating receptors may lack a domain which affects a self-inhibiting pathway in IL-10 signaling. There is evidence in IL-3R and EPO-R that there are cytoplasmic regions which, upon phosphorylation, normally downregulate responses to ligand binding. See D'Andrea, et al. (1991) *Mol. Cell. Biol.* 11:1980–1987; Sakamaki, et al. (1992) *EMBO J,* 11:3541–3549; and Sato, et al. (1993) *EMBO J.* 12:4181–4189.

Sensitivity describes an ability to induce proliferation of a target cell expressing the super-activating receptor. The present invention contemplates super-activating receptors exhibiting a sensitivity of at least about 5-fold higher than a wild-type receptor, generally at least about 10-fold higher, often at least about 20-fold higher, typically at least about 50-fold higher, usually at least about 70-fold higher, preferably at least about 100-fold higher, and in particular embodiments, at least about 150-fold higher or more.

Super-activating receptors will be useful for testing a sample for the presence of a ligand, e.g., human or mouse IL-10 or analogs thereof, in a sample. Kits exhibiting extremely high sensitivity are also contemplated for diagnostic purposes.

II. Receptor Variants

Isolated DNA encoding super-activating receptors can be readily modified by nucleotide insertions, deletions, and inversions. Receptor variants can also be produced by either genetic engineering methods or protein synthesis techniques. See, e.g., U.S. Ser. No. 08/110,683; U.S. Ser. No. 08/011,066; U.S. Ser. No. 07/989,792; Sambrook, et al. (1989); Ausubel, et al. (1987 and supplements); Cunningham, et al. (1989) *Science* 243:1330–1336; O'Dowd, et al. (1988) *J. Biol. Chem.* 263:15985–15992; Beaucage and Caruthers (1981) *Tetra. Letts.* 22:1859–1862; and Lechleiter, et al. (1990) *EMBO J.* 9:4381–4390; each of which is incorporated by reference. Additional methods will be apparent to a person having ordinary skill in the art in light of the teaching provided herein.

III. Nucleic Acids

This invention contemplates use of isolated nucleic acids, e.g., DNA, which encode these super-activating receptor components for IL-10-like ligands, e.g., peptides. Also included are substantially homologous sequences or fragments thereof. As indicated above, specific embodiments have demonstrated that deletion of regions 282-389, 282-414, and 282-458 of SEQ ID NO: 3 result in the super-activating phenotype. This suggests that this phenotype may be correlated with other deletions, e.g., beginning at 276 or 282; and ending at, e.g., 375, 389, 394, 406, 414, 422,435, or 458. Corresponding deletions in species or allelic variants will also exhibit similar properties. General descriptions of nucleic acids, their manipulation, and their uses are provided in the following references: U.S. Ser. No. 08/110,683; U.S. Ser. No. 08/011,066; U.S. Ser. No. 07/989,792; Kanehisa (1984) *Nuc. Acids Res.* 12:203–213; Wetmur and Davidson (1968) *J. Mol. Biol. 31:349–370;* Goodnow (1992) "Transgenic Animals" in Roitt (ed.) *Encyclopedia of Immunology* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987) (ed.) *Teratocarcinomas and Embryonic Stem Cells: A Practical Approach* IRL Press, Oxford; and Rosenberg (1992) *J. Clin. Oncol.* 10:180–99; each of which are incorporated by reference. Stringent conditions, in referring to homology in the hybridization context, will be stringent combined conditions of salt, temperature, organic solvents and other parameters typically controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. Additional aspects will be apparent to a person having ordinary skill in the art in light of the teachings provided herein.

IV. Making Receptor

A DNA encoding a super-activating IL-10 receptor is available by deletion mutagenesis of a wild type receptor available, e.g., in pMR29 (ATCC Deposit No. 69147) or pSW8.1 (ATCC Deposit No. 69146). The DNA can be expressed in a wide variety of expression systems as described in, e.g., U.S. Ser. No. 08/110,683; U.S. Ser. No. 08/011,066; U.S. Ser. No. 07/989,792; Pouwels, et al. (1985 and supplements) *Cloning Vectors; A Laboratory Manual,* Elsevier, N.Y.; Rodriquez, et al. (1988) (eds.) *Vectors: A Survey of Molecular Cloning Vectors and Their Uses,* Butterworths, Boston; Brosius, et al, (1988) "Expression Vectors Employing Lambda-, trp-, lac-, and Ipp-derived Promoters", in *Vectors: A Survey of Molecular Cloning Vectors and Their Uses,* (eds. Rodriguez and Denhardt) Butterworths, Boston, Chapter 10, pp. 205–236; Okayama, et al. (19885) *Mol. Cell Biol.* 5:1136–1142; Thomas, et al. (1987) *Cell* 51:503–512; and O'Reilly, et al. (1992) *Baculovirus Expression Vectors: A Laboratory Manual,* Freeman & Co., N.Y.; each of which is incorporated by reference. Additional teachings will be apparent to a person having ordinary skill in the art in light of the teachings provided herein.

V. Receptor Isolation

The DNA described above will be useful in producing high levels of super-activating receptor materials. Many of the uses will not require purification of the materials as their expression on cells will often be sufficient. However, these expressed receptors can be purified as described in, e.g., U.S. Ser. No. 08/110,683; U.S. Ser. No. 08/011,066; U.S. Ser. No. 07/989,792; Hochuli (1989) *Chemishe Industrie* 12:69–70; Hochuli (1990) "Purification of Recombinant Proteins with Metal Chelate Adsorbent" in Setlow (ed.) *Genetic Engineering, Principle and Methods* 12:87–98, Plenum Press, N.Y.; Crowe, et al. (1992) *OIAexpress; The High Level Expression & Protein Purification System* QUIAGEN, Inc., Chatsworth, Calif.; Ausubel, et al. (eds.) (1987) *Current Protocols in Molecular Biology;* Deutscher (1990) "Guide to Protein Purification" in *Meth. Enzymol.,* Vol. 182, and other volumes in series; and manufacturers' literature on use of protein purification products, e.g., Pharmacia, Piscataway, N.J., or Bio-Rad, Richmond Calif.; each of which is incorporated by reference. Additional methods will be apparent to a person having ordinary skill in the art in light of the teachings provided herein.

VI. Receptor Analogs

Derivatives of super-activating receptors are also encompassed by the present invention, particularly those exhibiting a feature of substantially increased proliferative response to IL-10 ligand binding relative to a natural receptor. These derivatives include sequence mutants, glycosylation variants, and covalent or aggregative conjugates with other chemical moieties. See, e.g., U.S. Ser. No. 08/110,683; U.S. Ser. No. 08/011,066; U.S. Ser. No. 07/989,792; Godowski, et al. (1988) *Science* 241:812–816; Beaucage and Caruthers (1981) *Tetra. Letts.* 22:1859–1862; Sambrook, et al. (1989) *Molecular Cloning: A Laboratory Manual* (2d ed.), Vols. 1–3, Cold Spring Harbor Laboratory; Merrifield (1963) *J. Amer. Chem. Soc.* 85:2149–2156; Merrifield (1986) *Science* 232: 341–347; Atherton, et al. (1989) *Solid Phase Peptide Synthesis: A Practical Approach,* IRL Press, Oxford; von Heijne (1992) *J. Mol. Biol.* 225:487–494; and Fasman, et al. (1990) *Trends in Biochemical Sciences* 15:89–92; each of which is incorporated by reference. Additional methods will be apparent to a person having ordinary skill in the art in light of the teachings provided herein.

VII. Antibodies

Various types of antibodies and antibody binding compositions can be raised to epitopes on super-activating receptors, particularly those which may distinguish super-activating variants from natural forms. For example, specific antigenic peptides which span the region of deletion will present epitopes that are absent in the natural versions. See, e.g., U.S. Ser. No. 08/110,683; U.S. Ser. No. 08/011,066; U.S. Ser. No. 07/989,792; *Miicrobiology*, Hoeber Medical Division, Harper and Row, 1969; Landsteiner (1962) *Specificity of Serological Reactions*, Dover Publications, New York; Williams, et al. (1967) *Methods in Immunology and Immunochemistry*, Vol. 1, Academic Press, N.Y.; Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, N.Y.; Kohler and Milsrein (1975) in *Nature* 256: 495–497; Huse, et al. (1989) "Generation of a Large Combinatorial Library of the Immunoglobulin Repertoire in Phage Lambda," *Science* 246:1275–1281; Ward, et al. (1989) *Nature* 341:544–546; U.S. Pat. Nos. 3,817,837; 3,850,752; 3,939,350; 3,996,345; 4,277,437; 4,275,149; 4,366,241; and Cabilly, U.S. Pat. No. 4,816,567; each of which is incorporated by reference. Additional methods will be apparent to a person having ordinary skill in the art in light of the teachings provided herein.

VIII. Other Uses of Receptors

Super-activating receptors will have many other uses such as carriers for a ligand, agonist, or antagonists; means to isolate other subunits of the receptor; or in diagnostic assays. See, e.g., U.S. Ser. No. 08/110,683; U.S. Ser. No. 08/011,066; U.S. Ser. No. 07/989,792; Hayashida, et al. (1990) *Proc. Nat'l Acad. Sci. USA* 87:9655–9659; Fodor, et al. (1991) *Science* 251:767–773; Parce, et al. (1989) *Science* 246:243–247; Owicki, et al. (1990) *Proc. Nat'l Acad. Sci. USA* 87:4007–4011; Lowenstein, et al. (1992) *Cell* 70:705–707; and Blundell and Johnson (1976) *Protein Crystallography*, Academic Press, N.Y. Diagnostic measurements other than proliferation are also contemplated. Assays include those which detect induction of transcription factors and/or DNA binding proteins, e.g., statl or p91. See, e.g., Pearse, et al. (1991) *Proc. Natl. Acad. Sci, USA* 88:11305–11309; and Pearse, et al. (1993) *Proc. Natl. Acad. Sci. USA* 90:4314–4318. Also contemplated are assays for molecules involved in signal transduction, e.g., phosphorylation of tyrosine kinases. See, e.g., Larner, et al. (1993) *Science* 261:1730–1733; and Lehmann, et al. (1994) *J. Immunol.* 153:165–172; each of which is incorporated by reference.

IX. Ligands: Agonists and Antagonists

The blocking of physiological response to IL-10-like peptides may result from the inhibition of binding of the ligand to the receptor, likely through competitive inhibition. Thus, in vitro assays of the present invention will often use isolated membranes from cells expressing a super-activating receptor or fragments attached to solid phase substrates. These assays will also allow for the diagnostic determination of the effects of either binding segment mutations and modifications, or ligand mutations and modifications, e.g.., ligand analogs. See, e.g., U.S. Ser. No. 08/110,683; U.S. Ser. No. 08/011,066; U.S. Ser. No. 07/989,792; each of which are incorporated by reference.

X. Kits

This invention also contemplates use of the super-activating IL-10 receptor, peptides, and their fusion products in a variety of diagnostic kits and methods, e.g., for detecting the presence of a ligand in a sample, e.g., mIL-10, hiL-10, or vIL-10. See, e.g., U.S. Ser. No. 08/110,683; U.S. Ser. No. 08/011,066; U.S. Ser. No. 07/989,792; U.S. Pat. No. 3,645,090; U.S. Pat. No. 3,940,475; Rattle, et al. (1984) *Clin. Chem.* 30(9):1457–1461; U.S. Pat. No. 4,659,678; and Rattle, et al. (1984) *Clin. Chem.* 30(9):1457–1461; each of which is incorporated by reference. Frequently the reagents for diagnostic assays are supplied in kits, so as to optimize the sensitivity of the assay. For the subject invention, depending upon the nature of the assay, the protocol, and the label, either labeled or unlabeled antibody, or labeled receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium having appropriate concentrations for performing the assay. One method for determining the concentration of IL-10 in a sample would typically comprise the steps of: expressing the transfected super-activating receptor on the surface of the host cell; contacting this cell with a sample containing the ligand, e.g., IL-10; and assaying for a biological effect, e.g., proliferation. The high sensitivity of the cells to a ligand can form the basis of a very sensitive assay.

XI. Therapeutic Applications

This invention provides reagents with significant therapeutic value. The super-activating IL-10 receptor, fragments thereof and antibodies thereto, along with compounds identified as having binding affinity to the super-activating IL-10 receptor, should be useful in the treatment of various conditions. See, e.g., autoimmune conditions, septic and toxic shock conditions, and infectious conditions. See, e.g., U.S. Ser. No. 08/110,683; U.S. Ser. No. 08/011,066; U.S. Ser. No. 07/989,792; Hsu, et al. (1992) *Int'l. Immunol.* 4:563–569; de Waal Malefyt, et al. (1991) *J. Exp. Med.* 174:1209–1220; Fiorentino, et al. (1991) *J. Immunol.* 147:3815–3822; Ishida, et al. (1992) *J. Exp. Med.* 175:1213–1220; Harada, et al. (1992) *J. Biol. Chem.* 267:22752–22758; Gilman, et al. (eds.) (1990) *Goodman and Gilman's: The Pharmacological Bases of Therapeutics*, 9th ed., Pergamon Press; *Remington's Pharmaceutical Sciences*, 17th ed. (1992), Mack Publishing Co., Easton, Penn.; and *The Merck Index*, Merck & Co., Rahway, N.J.; each of which is incorporated by reference.

XII. Additional Receptor Subunits

Various approaches would be useful for screening for accessory subunits of the IL-10 receptor. These approaches include both physical affinity methods, and activity screening. See, e.g., U.S. Ser. No. 08/110,683; U.S. Ser. No. 08/011,066; U.S. Ser. No. 07/989,792; Kitamura, et al. (1991) *Cell* 66:1165–1174; and Hara, et al. (1992) *EMBO J.* 11:1875–1884; each of which is incorporated by reference.

The broad scope of this invention is best understood with reference to the following examples, which are not intended to limit the invention to specific embodiments exemplified.

EXPERIMENTAL

EXAMPLE 1: General Methods

Some of the standard methods are described or referenced, e.g., in Maniatis, et al. (1982) *Molecular Cloning, A Laboratory Manual* Cold Spring Harbor Laboratory, Cold Spring Harbor Press; Sambrook, et al. (1989) *Molecular Cloning: A Laboratory Manual* (2d ed.), vols. 1-3, CSH Press, NY; Ausubel, et al., *Biology*, Greene Publishing Associates, Brooklyn, N.Y.; or Ausubel, et al. (1987 and Supplements) *Current Protocols in Molecular Biology* Greene/Wiley, New York; Innis, et al. (eds.)(1990) *PCR Protocols: A Guide to Methods and Applications* Academic Press, N.Y.; all of which are each incorporated herein by reference. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif.; which are incorporated herein by reference. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc., Chatsworth, Calif.: which are incorporated herein by reference.

Cell Lines and tissue culture.

Ba/F3 cells (provided by T. Kitamura, DNAX, Palo Alto, Calif.) were routinely grown in RPMI 1640 supplemented with 10% fetal bovine serum, 50 μM β-mercaptoethanol, and 10 ng/ml mIL-3 (Ba/F3 medium). Transfection of Ba/F3 cells was performed as described in Ho, et al. (1993) *Proc. Natl. Acad. Sci*, 90:11267–11271; and Kitamura, et al. (1991) *Proc. Natl. Acad. Sci*, 88:5082–5086. Ba/F3 transfectants were selected and maintained in Ba/F3 medium containing 1 mg/ml G418. Cell lines expressing recombinant IL-10R were isolated by repetitive cycles of cell sorting. See, e.g., Ho, et al. (1993) *Proc. Natl. Acad. Sci.* 90:11267–11271; and Liu, et al. (1994) *J. Immunol.* 152:1821–1829.

Fluorescence activated cell sorting (FACS)

Fluorescent activated cell sorting was performed using standard methods on a Becton-Dickinson FACStar PLUS. See, e.g., Shapiro (1988) *Practical Flow Cytometry* (2d ed.) Alan Liss, New York.

Cytokines and antibodies.

Recombinant CHO-derived human IL-10 and IL-5, as well as *E. coli*-derived human GM-CSF, IFN-γ, and mouse IL-10 were supplied by Schering-Plough Research Institute (SPRI), New Jersey. The specific biological activity of these preparations were $2.3\times10^7$ units/mg for hIL-10 and $1.6\times10^7$ units/mg for mIL-10 as measured by the MC/9 proliferation assay (see below). Recombinant hIL-6 was purchased from Genzyme (Cambridge, Mass.), though other commercial suppliers include, e.g., PeproTech, inc., Rocky Hill, N.J. Monoclonal antibodies to IL-10 and IL-5 were provided by J. Abrams (DNAX, Palo Alto, Calif.), see, e.g., Abrams, et al. (1992) *Immunol. Rev.* 127:5–24.

Binding Assays and Scatchard Analysis.

Approximately $5\times10^6$ cells for each cell line tested were pelleted by centrifugation at 200×g for 10 min, washed in PBS, and resuspended in 200 μl binding buffer (PBS, 10% fetal calf serum, 0.1% $NaN_3$) containing iodinated hIL-10 at a concentration of 100–500 pM. After incubation at 4° C. for two hours in a rotary mixer, the cells were centrifuged at 200×g for 10 min, resuspended in 100 μl binding buffer without labeled hIL-10, layered over 200 μl of a 1:1 mixture of dibutyl- and dioctyl-phthalate oils in elongated microcentrifuge tubes, centrifuged at 400×g for 5 min at 4° C., and quick frozen in liquid nitrogen. The cell pellets were then cut and counted in a Clinigamma 1272 counter (Pharmacia LKB). Non-specific binding was determined by performing the binding in the presence of 500 to 1000-fold molar excess unlabeled hIL-10. For saturation binding experiments, two-fold serial dilutions of approximately 600 pM solution of iodinated hIL-10 were used, with a parallel series done to determine non-specific binding. Scatchard analysis was performed on the data points obtained using the EBDA Program (Elsevier-Biosoft, Cambridge, U.K.). Antibody inhibition was done under the above binding conditions but with the addition of a 100-fold molar excess of each of the indicated monoclonal antibodies. Cytokine specificity was determined under similar conditions but with the addition of 500-fold molar excess of the cytokines indicated. Similar measurements can be made using the BIACORE apparatus (Pharmacia LKB) following manufacturer's recommendations.

EXAMPLE 2: Construction of deletion mutants.

Mutants carrying the open reading frame (ORF) of mIL-10R and the C-terminal deletion mutants Δ380-559, Δ402-559, and Δ433-559 were constructed by first removing the cytoplasmic domain and 3'-untranslated sequence by SmaI (located at Pro249)-NotI digestion of the mIL-10R cDNA pMR29 (ATCC Deposit No. 69147), see, e.g., Ho, et al. (1993) *Proc. Nat'l Acad. Sci.* 90:11267–11271. The excised fragment was then replaced by the appropriate polymerase chain reaction (PCR) amplified fragments which had been digested with SmaI and NotI. The PCR primers were:

Sense (S) primer: S1

5'-CCA GTG GTA CAT CCG GCA CCC GGG GAA GTT GCC-3'(SEQ ID NO: 7)

Antisense (AS) primers:

| | |
|---|---|
| Δ380-559 (AS1): | 5'-CGT CCG AAG CGC GGC CGC TCA TCA TCA CTG GTC CTG ATG GGT ATA TCC AAG CTG CTG-3' (SEQ ID NO: 8) |
| Δ402-559 (AS2): | 5'-CGT CCG AAG CGC GGC CGC TCA TCA TCA AGA TGC ATC CTG TGT GTA CTT AGG CTG CCC-3' (SEQ ID NO: 9) |
| Δ433-559 (AS3): | 5'-CGT CCG AAG CGC GGC CGC TCA TCA TCA TCT GGT CTG TTT CTG GTA GCC CTG GAA TGT-3' (SEQ ID NO: 10) |
| ORF: | 5'-CGT CCG AAG CGC GGC CGC TCA TCA TCA TTC TTC TAC CTG CAG GCT GGA GAT CAA CGG CAG-3' (SEQ ID NO: 11) |

The ligation mixture was transformed into *E. coli* and the plasmid isolated from individual colonies was analyzed. Each selected clone was then sequenced to confirm the deletion. For one C-terminus deletion mutant (Δ483-559) and all N-terminus deletion mutants: Δ282-389, Δ282-414, and Δ282-458, the DraIII site (Val281) in mIL-10R was used instead of SmaI. The primers for each construction were:

Sense primer: S2

5'-CCC GAT GCC ATT CAC ATC GTG GAC CTG GAG GTT TTC CC-3'(SEQ ID NO: 12)

Antisense primers:

| | |
|---|---|
| Δ282-389 (AS4): | 5'-CGT CCG AAG CAC ATC GTG TCT CCA GGG CAG CCT AAG TAC ACA CAG GAT GCA TCT GCC-3' (SEQ ID NO: 13) |
| Δ282-414 (AS5): | 5'- CGT CCG AAG CAC ATC GTG GAG GAG AAA GAC CAA GTC ATG GTG ACA TTC CAG GGC TAC CAG-3' (SEQ ID NO: 14) |
| Δ282-458 (AS6): | 5'-CGT CCG AAG CAC ATC GTG GGG GTA CAC CTG CAG GAT GAT TTG GCT TGG CCT CCA CCA GCT-3' (SEQ ID NO: 15) |
| Δ483-559 (AS7): | 5'- CGT CCG AAG CGC GGC CGC TCA TCA TCA AGA CTC CTG TTT CAA ATA ACC TGC GGC CAG-3' (SEQ ID NO: 16) |

PCR amplification was at 94° C. for 2 min (1 cycle); followed by 30 cycles of: 94° C., 30 sec; 55° C., 30 sec; 72° C., 1 min Similar methods will be useful for making other deletion variants as desired, both in the mouse and other mammalian receptors.

EXAMPLE 3: Internalization of IL-10.

Cells (~1.5-2×10$^6$ in 150–250 ml) were incubated with 700 pM $^{125}$I-hIL-10 in binding buffer without sodium azide for 2–60 min at 37° C. A 50 μl aliquot of the binding reaction was added to 150 ml 0.1M NaCl, 80 mM sodium citrate pH 4.0 for 10 min at room temperature, conditions predetermined to maximize cell viability (>90%) and removal of receptor-bound IL-10, yet minimize nonspecific binding of $^{125}$I-hIL-10. The cells were then pelleted through an oil pad and assessed for cell-associated and free $^{125}$I cpm as described above. Nonspecific cell-associated cpm in samples containing unlabeled hIL-10 competitor were subtracted to obtain specific cell-associated cpm. Results were compared to the amount of $^{125}$I-hIL-10 bound at 4° C. for 80–90 min in the presence of sodium azide (no internalization), with or without excess hIL-10 competitor, and expressed as % of the specific cpm bound during the 4° C. incubation.

EXAMPLE 4: Proliferation Assay.

Cells expressing wild-type and mutant mIL-10R were tested for responsiveness to IL-10 in a cell proliferation assay as described in Ho, et al. (1993) *Proc. Nat'l. Acad. Sci.* 90:11267–11271; and Liu, et al. (1994) *J. Immunol.* 152:1821–1829, with a colorimetric assay using Alamar Blue (Alamar Biosciences, Sacramento, Calif.). The concentration of IL-10 inducing a half-maximal response was defined as 1 unit/ml. In some experiments, cells were washed twice and introduced into cultures where fetal calf serum (FCS) was substituted with a mixture of 0.5 mg/ml BSA, 2.5 μg/ml linoleic acid, 5 μg/ml insulin, 5 μg/ml transferrin, and 5 ng/ml sodium selenite. In cultures where insulin was also omitted, supplements were 0.5 mg/ml BSA, 2.5 μg/ml linoleic acid, and 50 μg/ml transferrin.

Example 5: Induction of DNA-binding proteins

Induction of transcription factors, i.e., p91 (stat1) are also assayed. Ba/F3 cells transfected with super-activating receptors are stimulated with IL-10 and nuclear extracts are prepared. See, e.g., Larner, et al. (1993) *Science* 261:1730–1733. Nuclear extracts are then tested in electrophoretic mobility shift assays for the presence of proteins that bind to $^{32}$P-labeled double stranded oligonucleotide containing various response elements, e.g., IFNγ response sequence. See, e.g., Pearse, et al. (1991) *Proc. Natl. Acad. Sci. USA* 88:11305–11309; and Pearse, et al. (1993) *Proc. Natl. Acad. Sci. USA* 90:4314–4318. The super-activating receptors will likely be more sensitive, with regard to induction of DNA binding proteins, from a given dose of ligand.

Example 6: Phosphorylation of tyrosine kinases

Phosphorylation of tyrosine kinases, e.g., JAK1 and TYK2, is measured by starvation of Ba/F3 cells transfected with super-activating receptors, e.g., in RPMI+0.5% bovine serum albumin (BSA) for 4–5 hours at 37° C. These cells are then washed once with RPMI 1640 and resuspended, e.g., in RPMI 1640+0.1% BSA (2×10$^7$ cells/ml). Cells are incubated with or without IL-10 (or IL-3) for 10 min at 37° C. Cells are then pelleted and lysed (2×10$^7$/ml) in lysis buffer (1% Triton X100, 10 mM iodoacetamide, 150 mM NaCl, 10 mMTris-Cl, pH 7.5, 1 mM sodium orthovanadate, 10 mM sodium fluoride, 2 mM EDTA, 30 mM phosphatase substrate (Sigma Chemical Co., St. Louis, Mo.); 100 μg/ml TPCK, 1 mM PMSF, 10 μg/ml each aprotinin, leupeptin, and pepstatin A) by rocking at 4° C. for 30 min. After removal of cell debris by centrifugation, the lysates are incubated with anti-JAK1 (UBI, Lake Placid, N.Y.) or anti-TYK2 (Santa Cruz Biotechnology, Santa Cruz, Calif.) antibodies respectively overnight at 4° C. The mixture is then incubated with 100 μl of protein G/A Plus agarose (Santa Cruz Biotechnology) at 4° C. for 2 hr. After three washes, the agarose is boiled with 2× Laemmli's sample buffer for 10 min before applying to 7.5% SDS-PAGE. Proteins are subsequently electro-transferred onto a NitroPlus membrane (Micron Separations, Inc., Westboro, Mass.). After blocking with Tris-buffered saline (TBS) containing 3% BSA at 37° C. for 30 min, the membranes are incubated with the anti-kinase antibodies to visualize protein, or with anti-phosphotyrosine antibody 4G10 (UBI) in TBS with 0.1% Tween for 2 hr. After several washes the results are visualized by incubation with peroxidase-conjugated anti-rabbit Ig (Promega, Madison, Wis.) or anti-mouse Ig (Amersham, Arlington Heights, Ill.) and subsequent use of the ECL detection system (Amersham). See Larner, et al. (1993) *Science* 261:1730–1733. The super-activating receptors will likely produce a greater level of phosphorylation for a given amount of ligand.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A super-activating mammalian IL-10 receptor protein wherein said receptor is:

a) a wild-type IL-10R possessing a cytoplasmic membrane proximal deletion; and b) is encoded by a nucleic acid which is capable of hybridizing to a nucleic acid of SEQ ID NO: 1 or 4 at 45° C. and 400 mM salt.

2. The super-activating receptor of claim 1, wherein said wild-type receptor corresponds to the amino acid sequence of SEQ ID NO: 3, and said deletion is selected from the group consisting of:

a) Asp282 and Asn389, inclusive;

b) Asp282 and Pro414, inclusive;

c) Asp282 and Leu458, inclusive;

d) Asp276 and Thr375, inclusive;

e) Asp276 and Pro394, inclusive; and f) Asp276 and Ala435, inclusive.

3. A method of testing for a ligand of a super-activating mammalian IL-10 receptor in a sample comprising:

a) contacting said sample with a cell expressing a super-activating mammalian IL-10 receptor of claim 2; and b) detecting signaling mediated by ligand binding after said contacting.

4. The method of testing of claim 3, wherein said cell is a mouse cell.

5. A nucleic acid encoding said protein of claim 2.

6. The super-activating receptor of claim 1, wherein said receptor has a higher sensitivity to a ligand than a wild-type IL-10 receptor.

7. The super-activating receptor of claim 6, wherein said sensitivity is assayed by proliferation.

8. The super-activating receptor of claim 6 wherein said higher sensitivity is at least about 5 fold higher to said ligand.

9. The super-activating receptor of claim 6, wherein said higher sensitivity is at least 20 fold higher to said ligand.

10. A cell comprising a super-activating receptor of claim 1.

11. The cell of claim 10, which is a mouse cell.

12. The super-activating mammalian IL-10 receptor protein of claim 1, wherein said SEQ ID NO: is 4.

13. A kit comprising a compartment containing a super-activating mammalian IL-10 receptor protein of claim 1 expressed on a cell.

14. The kit of claim 13, wherein said hybridizing is at:

a) 55° C.; and/or b) 200 mM salt.

15. The receptor of claim 1, wherein said hybridizing is at:

a) 55° C.; and/or b) 200 mM salt.

16. A nucleic acid comprising a sequence which a) encodes a super-activating mammalian IL-10 receptor possessing a cytoplasmic membrane proximal deletion; and b) hybridizes to a nucleic acid of SEQ ID NO: 1 or 4 at 45° C. and 40 mM salt.

17. The nucleic acid of claim 16 in an expression vector.

18. The nucleic acid of claim 17, wherein said nucleic acid is:

a) operably linked to a genetic control element of an expression vector; and/or b) transfected into an appropriate host cell.

19. The nucleic acid of claim 18, wherein said host cell is a mouse cell.

20. A method of producing a super-activating mammalian IL-10 receptor protein comprising a step of expressing a nucleic acid of claim 16 in a cell.

21. The nucleic acid of claim 20, wherein said hybridizing is at:

a) 55° C.; and/or b) 200 mM salt.

22. A cell comprising said nucleic acid of claim 12.

23. The nucleic acid of claim 16, wherein said nucleic acid hybridizes at:

a) 55° C.; and/or b) 200 mM salt.

24. A kit comprising a compartment containing a nucleic acid suitable for transfection into a cell, wherein said nucleic acid:

a) encodes a super-activating mammalian IL-10 receptor protein possessing a cytoplasmic membrane proximal deletion; and b) hybridizes to a nucleic acid of SEQ ID NO: 1 or 4 at 45° C. and 400 mM salt.

25. The kit of claim 24, wherein said cell is a mammalian cell.

26. The kit of claim 24 wherein said hybridizing is at:

a) 55° C.; and/or b) 200 mM salt.

* * * * *